(12) United States Patent
Bierman et al.

(10) Patent No.: US 8,251,956 B2
(45) Date of Patent: Aug. 28, 2012

(54) SECUREMENT DEVICE

(75) Inventors: Steven Bierman, Del Mar, CA (US); Richard Pluth, San Diego, CA (US)

(73) Assignee: Venetec International, Inc., Covington, GA (US)

( * ) Notice: Subject to any disclaimer, the term of this patent is extended or adjusted under 35 U.S.C. 154(b) by 616 days.

(21) Appl. No.: 12/446,093

(22) PCT Filed: Oct. 18, 2007

(86) PCT No.: PCT/US2007/081846
§ 371 (c)(1),
(2), (4) Date: Apr. 17, 2009

(87) PCT Pub. No.: WO2008/051810
PCT Pub. Date: May 2, 2008

(65) Prior Publication Data
US 2010/0324491 A1 Dec. 23, 2010

Related U.S. Application Data

(60) Provisional application No. 60/853,365, filed on Oct. 20, 2006.

(51) Int. Cl.
*A61M 25/02* (2006.01)
(52) U.S. Cl. .................................................. 604/174
(58) Field of Classification Search .................. 604/174, 604/19, 48, 177, 178, 180, 93.01; 606/157, 606/158; 248/74.1, 74.2, 74.4; 251/9, 10
See application file for complete search history.

(56) References Cited

U.S. PATENT DOCUMENTS

| | | | | |
|---|---|---|---|---|
| 4,699,616 A * | 10/1987 | Nowak et al. | ................. | 604/180 |
| 5,722,959 A * | 3/1998 | Bierman | ....................... | 604/174 |
| 6,387,076 B1 * | 5/2002 | Landuyt | ....................... | 604/174 |
| 6,673,046 B2 * | 1/2004 | Bierman et al. | .............. | 604/174 |
| 7,014,627 B2 * | 3/2006 | Bierman | ....................... | 604/174 |
| 7,303,548 B2 * | 12/2007 | Rhad et al. | .............. | 604/164.08 |
| 7,635,355 B2 * | 12/2009 | Bierman | ....................... | 604/174 |
| 2002/0188255 A1 * | 12/2002 | Bierman et al. | .............. | 604/174 |
| 2005/0027258 A1 * | 2/2005 | Bierman et al. | .............. | 604/174 |
| 2005/0192539 A1 * | 9/2005 | Bierman et al. | .............. | 604/174 |
| 2006/0135944 A1 * | 6/2006 | Bierman | ....................... | 604/500 |
| 2010/0298777 A1 * | 11/2010 | Nishtala | ....................... | 604/174 |

OTHER PUBLICATIONS

International Search Report and Written Opinion issued in PCT/US2007/81846 dated Apr. 10, 2008.

* cited by examiner

*Primary Examiner* — Bhisma Mehta
*Assistant Examiner* — Michael J Anderson
(74) *Attorney, Agent, or Firm* — Knobbe Martens Olson & Bear LLP

(57) ABSTRACT

A securement device holds a medical article such as a catheter hub in position upon the body of a patient and at least inhibits longitudinal movement of the medical article. The securement device includes a retainer and at least one anchor pad. The retainer includes a metallic insert having barbs or teeth extending into a central channel. The metallic barbs or teeth dig into the retained catheter hub. The metal insert springs open as the hub is inserted in to the device and retains the hub by virtue of its metallic barbs.

22 Claims, 23 Drawing Sheets

SECUREMENT DEVICE

RELATED APPLICATIONS

This application is a national stage under 35 U.S.C. §371 of International Application No. PCT/US2007/081846, filed Oct. 18, 2007, now published as WO2008/051810, which claims priority under 35 U.S.C. §119(e) to U.S. Provisional Application Ser. No. 60/853,365, filed on Oct. 20, 2006, which is hereby incorporated by reference in its entirety.

BACKGROUND OF THE INVENTION

1. Field of the Invention

This invention relates to a securement system used to attach a medical article to a patient.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical article properly positioned for the duration of treatment, the catheter or medical article can be secured to the patient in a variety of ways. Most commonly, this involves taping or suturing the catheter or medical article to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin. Such repeated applications of tape over the catheter or medical article can additionally lead to the build up of adhesive residue on the outer surface of the catheter or medical article. This residue can result in contaminants adhering to the medical article itself, increasing the likelihood of infection of the insertion site. This residue can also make the catheter or medical article stickier and more difficult to handle for healthcare providers.

Suturing also carries risk, both to healthcare workers and patients. Healthcare workers can suffer accidental needlestick injury, which may expose them to hepatitis, HIV, and other pathogens. Patients can suffer local or even systemic infection from suture, as well as scarring and pain.

Therefore, an improved system that obviates tape and suture is desired for securement of catheters and other medical articles.

SUMMARY OF THE INVENTION

In one aspect, a retainer for securing a medical article includes a body portion, the body portion including a channel extending in a longitudinal direction therethrough, the channel being configured to accept at least a portion of a medical article, at least one barb extending inwardly into the channel, the barb being configured to move independent of the body portion, the barb pressing against the medical article so as to inhibit longitudinal motion of the medical article when the medical article is placed within the channel, and at least one anchor configured to fit against the skin of the patient, the anchor supporting the body portion.

In one aspect, a securement device includes a body portion, the body portion including resiliently deformable sidewalls which cooperate to define a channel extending in a longitudinal direction through the body portion and configured to accept at least a portion of a medical article therein, the sidewalls being deformable laterally outward to permit passage of the medical article through an opening therebetween, and at least one rigid barb extending inwardly into the channel, the barb being configured to interact with an exterior surface of the medical article to inhibit movement of the medical article relative to the body portion.

In one aspect, a securement device for retaining a medical article includes a channel dimensioned so as to retain at least a portion of the medical article, the channel being at least partially defined by a pair of opposing walls, and an insert disposed within the channel, the insert including a first barb, a second barb, and a receiving space therebetween for retaining a portion of the medical article when the portion of the medical article is retained within the channel, where the first and second barbs extending inwardly into the channel, the insert being biased such that the barbs remain in a first position when no portion of a medical article is retained within the receiving space, and the barbs being movable to a second position to accommodate at least a portion of a medical article disposed within the receiving space, the barbs being farther away from a central axis of the channel than the first position.

In one aspect, a retainer includes a body portion, the body portion including a channel extending in a longitudinal direction therethrough, where the body portion includes a first material, and a barb, where a portion of the barb extends inwardly into the channel so as to deform an outer surface of a medical article retained within the channel, the barb including a second material, the second material being harder than the first material, at least one footing supporting the body portion.

DETAILED DESCRIPTION OF THE PREFERRED EMBODIMENTS

The following description and the accompanying figures, which describe and show the preferred embodiments, are made to demonstrate several possible configurations that a securement system can take to include various aspects and features the invention. Those of skill in the art will recognize that the disclosed aspects and features of the invention are not limited to any particular embodiment of a securement system, and securement systems, which include one or more of the inventive aspects and features herein described, can be designed for use with a variety of medical articles.

Figure 1:
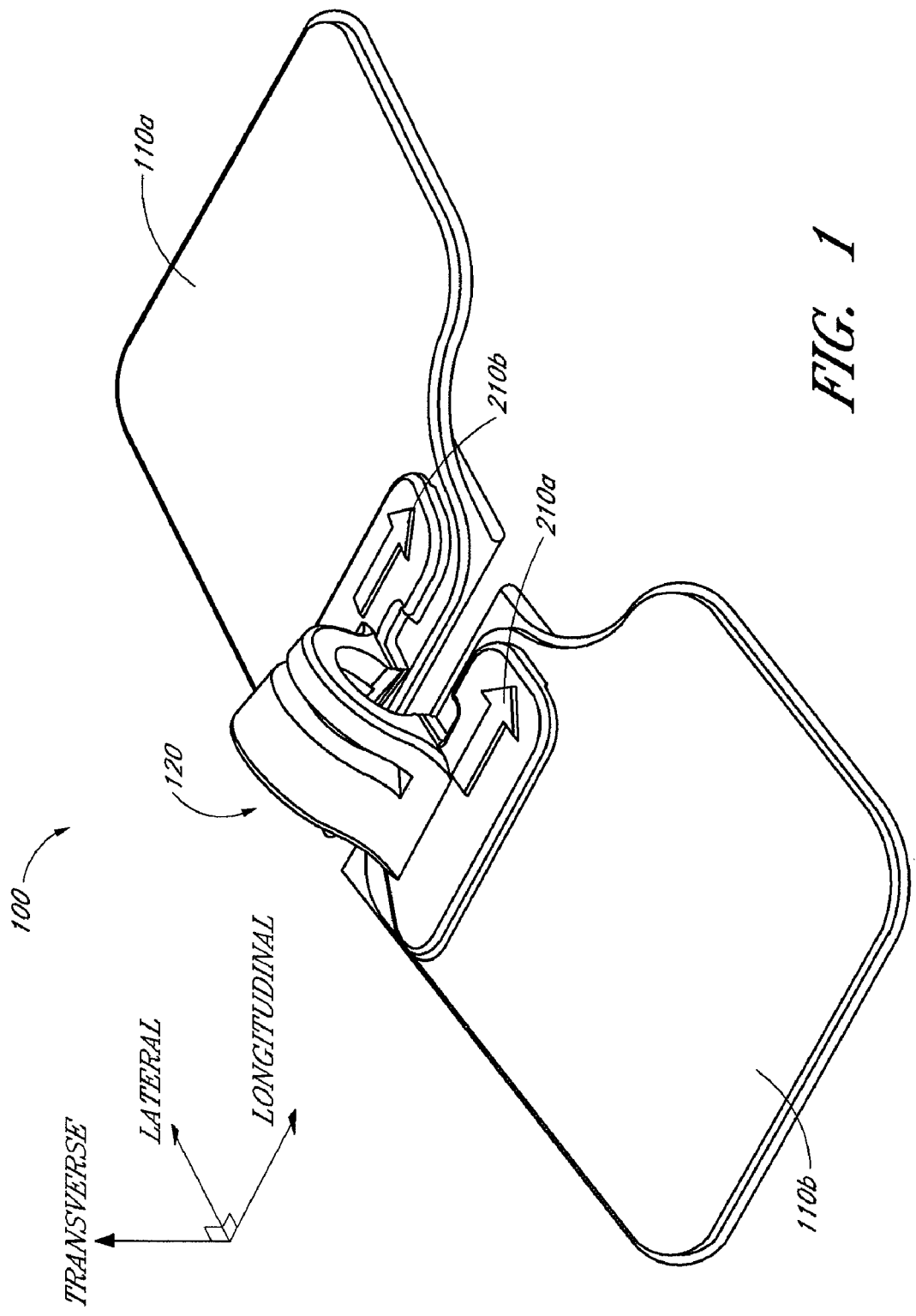
FIG. 1 is a perspective view of the securement device configured in accordance with a preferred embodiment of the present invention.

To assist in the description of these components of the securement system, the following coordinate terms are used (see FIG. 1). A "longitudinal axis" is generally parallel to a portion of the medical article retained by the securement system, as well as parallel to the axis of a channel of the retainer, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or connector fitting, and therefore is substantially synonymous with the term "longitudinal" as used herein.

Also, the terms "proximal" and "distal", which are used to describe the present securement system, are used consistently with the description of the exemplary applications (i.e., the illustrative examples of the use applications). Thus, proximal and distal are used in reference to the center of the patient's body. The terms "upper," "lower," "top," "bottom," "underside," "upperside" and the like, which also are used to describe the present securement system, are used in reference to the illustrated orientation of the embodiment. For example, the term "upperside" is used to describe the portion of the retainer that is located above a lateral axis that passes through the axis of the channel. The term "underside" is used to describe the portion of the retainer that is located below a lateral axis that passes through the axis of the channel. Brief introductions to some of the features, which are common to the described embodiments of the securement systems, are now described. In the illustrated embodiment, the arrows on the securement device point in the direction toward the insertion site (i.e., in the proximal direction).

The preferred embodiments of the present invention advantageously provide a medical line securement system for securing a medical article to a patient. The medical article preferably has an elongated body. The elongated body cooperates with a retainer to arrest movement of the medical article in longitudinal, lateral, and transverse directions when placed within the retainer.

In certain of the embodiments described below, the retainer has a body member which includes an inverted channel formed therethrough. The inverted channel has a longitudinal access opening located on an underside of the retainer to allow ingress or egress of the medical article. The medical article is installed or removed from the underside of the retainer via this access opening. Such an arrangement allows the medical provider to align at least a portion of the medical article with the retainer prior to fixing the retainer to the patient's skin. In this way, the inverted channel retains a portion of the medical article. In other embodiments described below, the retainer has a body member including a non-inverted channel formed therethrough. In such embodiments, the medical article may be installed or removed from the upper side of the medical article, such that the retainer is disposed between the medical article and the patient's skin. In this embodiment, the medical article may be installed or removed after fixing the retainer to the patient's skin.

The retainer includes at least one insert that is disposed on the retainer and in the wall of the inverted or non-inverted channel. With this construction, the insert inhibits longitudinal movement of the medical article when the retained portion is positioned against the insert. The insert may be separately or integrally formed with the body of the retainer.

The retainer of each embodiment described below further includes at least one support that is preferably disposed on the underside of the retainer at a position lower than the access opening. With this construction, the retainer holds the retained portion of medical article away from the patient's skin, when the retained portion is positioned within the retainer channel, to avoid chaffing or excoriating the skin. The support in each of the illustrated embodiments includes left and right mounting wings that are integral with the body member and are attached to left and right anchor pads. The lower surfaces of the left and right anchor pads attach to the patient's skin.

The retainer and anchor pad(s) also can have other constructions in order to inhibit contact between the skin and the retainer, as well as between the skin and the retained portion of the medical article. For example, the anchor pads can be thicker, in which case the mounting wings can be located higher on the retainer body.

To facilitate a complete understanding of the embodiments, the remainder of the detailed description describes the securement system with reference to the figures, wherein like elements among the embodiments are referenced with like numerals throughout the following description.

Figure 1A:
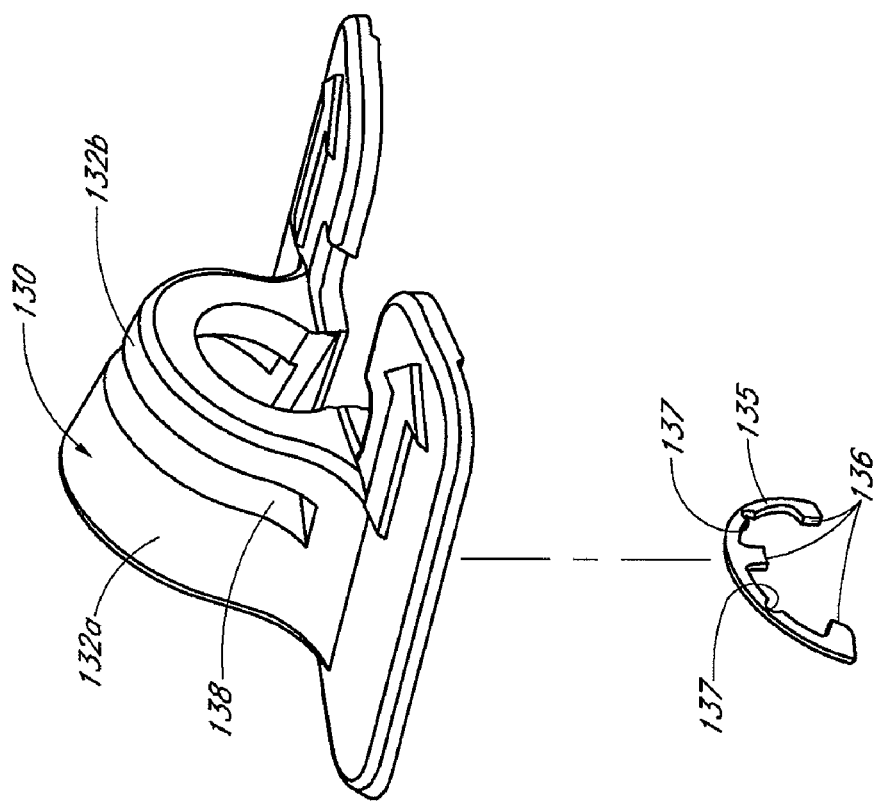
FIG. 1A is an exploded perspective view of the securement device of FIG. 1 with an insert separated from a body of the securement device.

FIG. 1 is a perspective view of a securement device 100 configured in accordance with an embodiment of the present invention. FIG. 1A is an exploded perspective view of the securement device 100 of FIG. 1 with an insert 135 separated from a body 130 of the securement device 100. The insert 135 is preferably made of a metallic or ceramic material and includes one or more barbs or teeth 136. In the illustrated embodiment the insert 135 includes three barbs: a central barb 136a and two lower barbs 136b,c, as well as two notches 137. In the illustrated embodiment, the insert further includes longitudinal grooves or notches 137. The grooves 137 are preferably disposed around the inside circumference of the insert 135. In certain embodiments, the notches 137 may facilitate motion of the lower barbs 136b and 136c relative to the central barb 136a, such as the spreading of the insert to accept the body of the medical article to be retained. The securement device 100 overcomes the challenges presented by medical articles such as catheter hubs that do not include a push tab or other radially or outwardly extending member. The insert 135 springs open as the medical article is inserted in to the insert 135 and retains the medical article by virtue of its barbs 136a,b,c. In certain embodiments, the upper barb 136a may remain substantially fixed while the lower barbs 136b and 136c spread outward slightly to accommodate ingress of the body of the medical article and then press inward on the medical article to provide a retention force.

Figure 2:
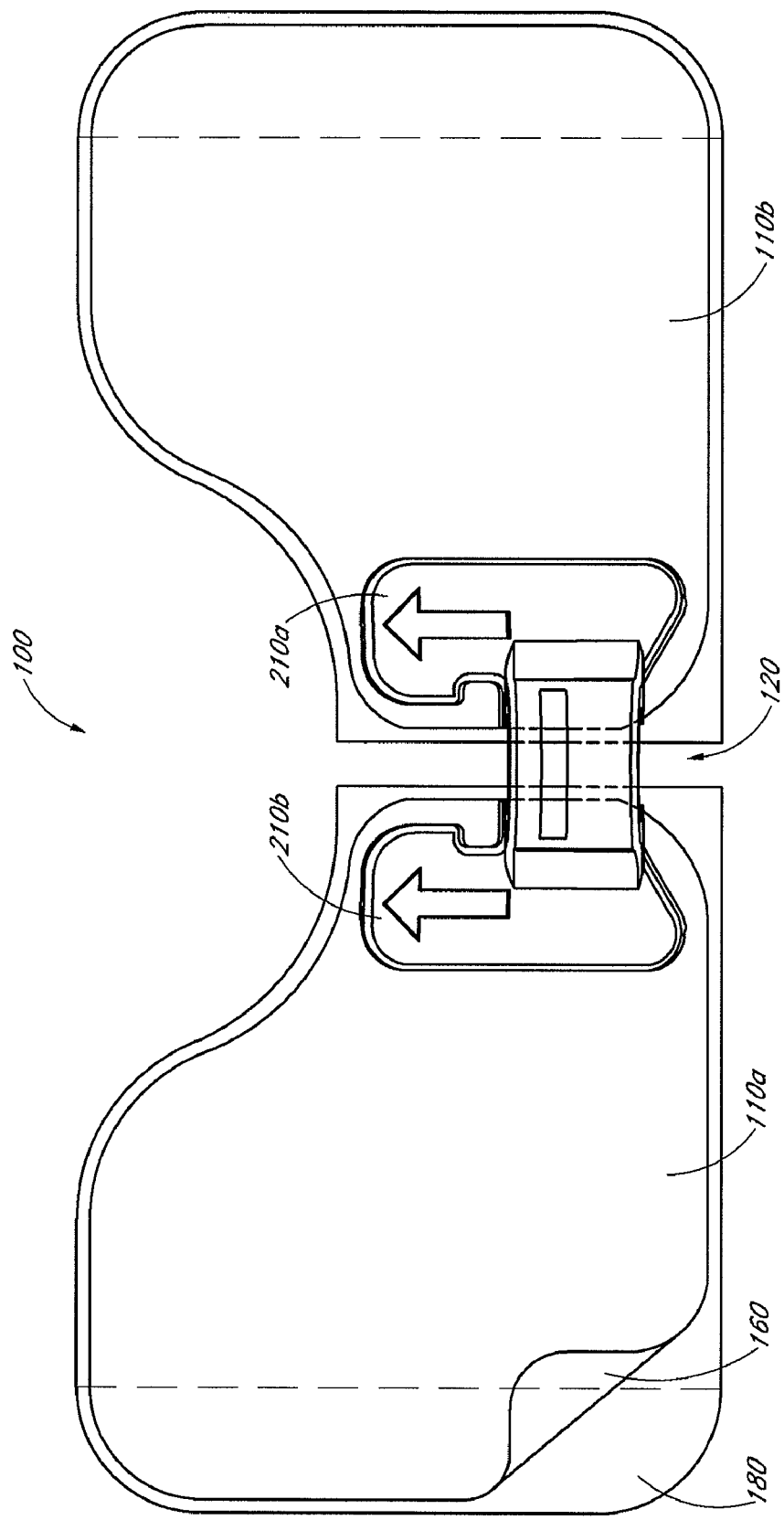
FIG. 2 is a top plan view of the securement device of FIG. 1 that includes a retainer and anchor pads.

FIG. 2 is a top plan view of the securement device 100 of FIG. 1. As shown in FIGS. 1, 1A, and 2, the illustrated securement device 100 comprises three main components: two anchor pads 110(a), 110(b) and a retainer 120. The illustrated retainer 120 includes a left footing/mounting wing 210(a) and right footing/mounting wing 210(b). Each mounting wing is disposed upon the respective one of the anchor pads 110(a), 110(b). The mounting wings 210(a), 210(b) extend in a lateral direction away from a center of the retainer 120.

As noted above, the securement device 100 can form a component of a catheterization or securement system that also includes one or more medical articles, such as connector fittings, catheters, hubs, catheter adaptors, fluid supply lines, or other articles suitable for securement via the anchor pads and retainer. An opening in the retainer 120 is aligned with the medical article. The medical article is inserted between the anchor pads 110(a), 110(b), through the opening, and into the retainer 120. Teeth or barbs 136a,b,c of the insert 135 grip the medical article.

The anchor pads 110(a), 110(b) are then secured to the skin of the patient, generally by an adhesive disposed upon the bottom surface of the pads. In this way, the retainer 120 secures the medical article to the patient. Thus, the retainer at least restricts, if not prevents, lateral and transverse movement of the retained section of the medical article. Additional features of the securement device 100 can restrict, if not prevent, longitudinal and rotational movement of the retained section of the medical article. The embodiment illustrated is preferably for use with a medical article as described with reference to FIG. 13. The embodiments of the anchor pad and the retainer are described in more detail below.

Anchor Pad

Figure 3:
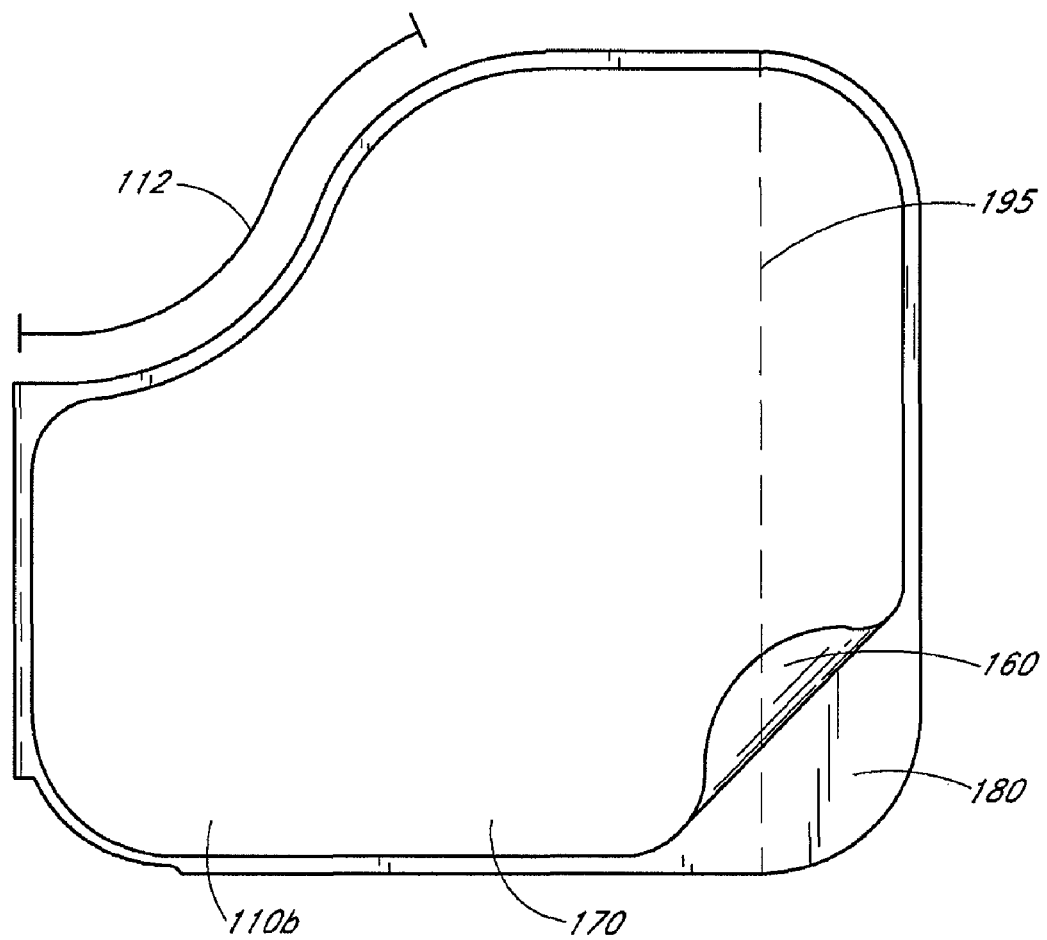
FIG. 3 is a top plan view of a right anchor pad of FIG. 2.
Figure 4:
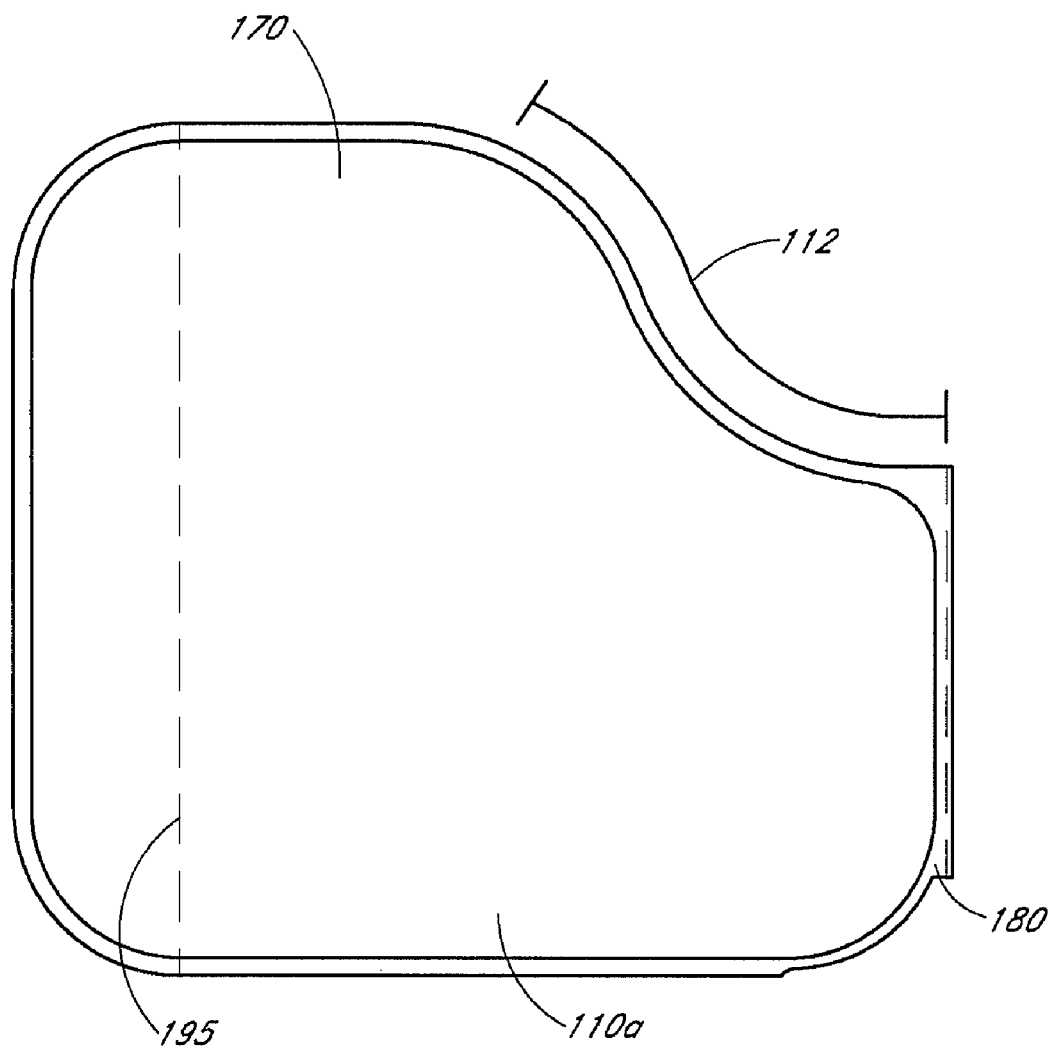
FIG. 4 is a top plan view of a left anchor pad of FIG. 2.

FIGS. 3 and 4 illustrate the anchor pads 110(b), 110(a), respectively, apart from the rest of the securement device 100 shown in FIG. 2. The general structure of each anchor pads 110(a), 110(b) comprises a generally rectangular shape with a scalloped region 112 located at a corner of each anchor pad. The scalloped configuration eases the process of aligning the securement device 100 with a catheter insertion site in the patient's skin. Although only a single shape of the anchor pad is illustrated in FIGS. 3 and 4, those of skill in the art will recognize that a variety of shapes can be used.

Each anchor pad 110 desirably comprises a laminate structure with an upper plastic (e.g., Tricot woven polyester), paper or foam layer (e.g., closed-cell polyethylene foam) and a lower adhesive layer. The lower adhesive layer constitutes a lower surface 160 of the anchor pad. The lower surface 160 desirably is a medical-grade adhesive and can be either diaphoretic or nondiaphoretic, depending upon the particular application. Such foam with an adhesive layer is available commercially from Avery Dennison of Painsville, Ohio. While not illustrated, the anchor pads 110(a), 110(b) can include suture holes in addition to the adhesive layer to further secure the anchor pad to the patient's skin.

In other variations, a hydrocolloid adhesive or zinc oxide-based adhesive can advantageously be used upon the anchor pads 110(a), 110(b) for attaching the anchor pads to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

In another variation, each anchor pad 110(a), 110(b) comprises a laminate structure with an upper woven layer and a lower adhesive layer. The upper layer can be polyester or other suitable polymer or textile materials. One particular suitable material is woven polyester available commercially under the name "Tricot" from Tyco. The lower adhesive layer constitutes the lower surface 160 of the anchor pad. The lower surface desirably is a medical-grade adhesive and can be either diaphoretic or nondiaphoretic, depending upon the particular application.

A surface of the upper foam layer constitutes an upper surface 170 of the anchor pads 110(a), 110(b). The upper surface 170 can be roughened by corona-treating the foam with a low electric charge. The roughened or porous upper surface can improve the quality of the adhesive joint (which is described below) between the mounting wings 210 and the anchor pads 110. In a further variation, the flexible anchor pad can comprise an upper paper or other woven or nonwoven cloth or plastic layer in lieu of a roughened upper foam surface.

The anchor pads 110(a), 110(b) preferably are arranged with respect to the retainer 120 such that the tip of the medical article does not extend beyond the front edge of the mounting wings 210 when the medical article is properly inserted within the retainer 120.

As illustrated in FIG. 3, a removable paper or plastic release liner 180 desirably covers the adhesive lower surface 160 before use. The liner 180 preferably resists tearing and desirably is divided into a plurality of pieces to ease attachment of the pad to a patient's skin.

The liner 180 comprises a folded over portion to define a pull tab 195 (see FIG. 3 or 4). The pull tab can be utilized to remove the paper or plastic release liner 180 from their adhesive lower surface 160 during application. A healthcare provider uses the pull tab 195 by grasping and pulling on it so that the liner 180 is separated from the lower surface 160. The pull tab 195 overcomes any requirement that the healthcare provider pick at a corner edge or other segment of the liner in order to separate the liner from the adhesive layer.

The pull tab 195 of course can be designed in a variety of configurations. For example, the pull tab 195 can be located along a center line of the anchor pad 110; or alternatively, the pull tab can be located along any line of the anchor pad 110 in order to ease the application of the anchor pad onto the patient's skin at a specific site.

The fold that forms the pull tab 190 preferably occurs medially beyond the inner (medial) edge on each anchor pad 110(a), 110(b), as best seen in FIG. 2, rather than at the inner edge of the anchor pad 110(a), 110(b). Thus, the spacing between the folds of the release liners 180 is less than the spacing between the inner edges of the anchor pads 110(a), 110(b). The projection of the release linear beyond the anchor pad inner edge provides an area onto which any adhesive, which is used to attach the retainer to the anchor pad, can run while lessening the occurrence of such adhesive contacting the fold. Cracks often occur at the fold and presence of adhesive in such cracks can create delamination of the release liner and incomplete removal of the release linear when peeled away from the corresponding anchor pad 110(a), 110(b).

Additionally, the distal side of each release linear is cut to increase a "view window" through which a healthcare provider can see when aligning the retainer over the medical article (e.g., the catheter hub and/or the connector fitting). Preferably, the resulting relief originates from the inner edge of the release linear generally at a right angle thereto and then transitions into a shape that generally matches the shape of the adjacent region of corresponding anchor pad 110(a), 110(b). The initial right-angle cut of this relief reduces instances of the release linear ripping when properly pulled in the lateral direction away from the retainer 120.

Retainer

Figure 5:
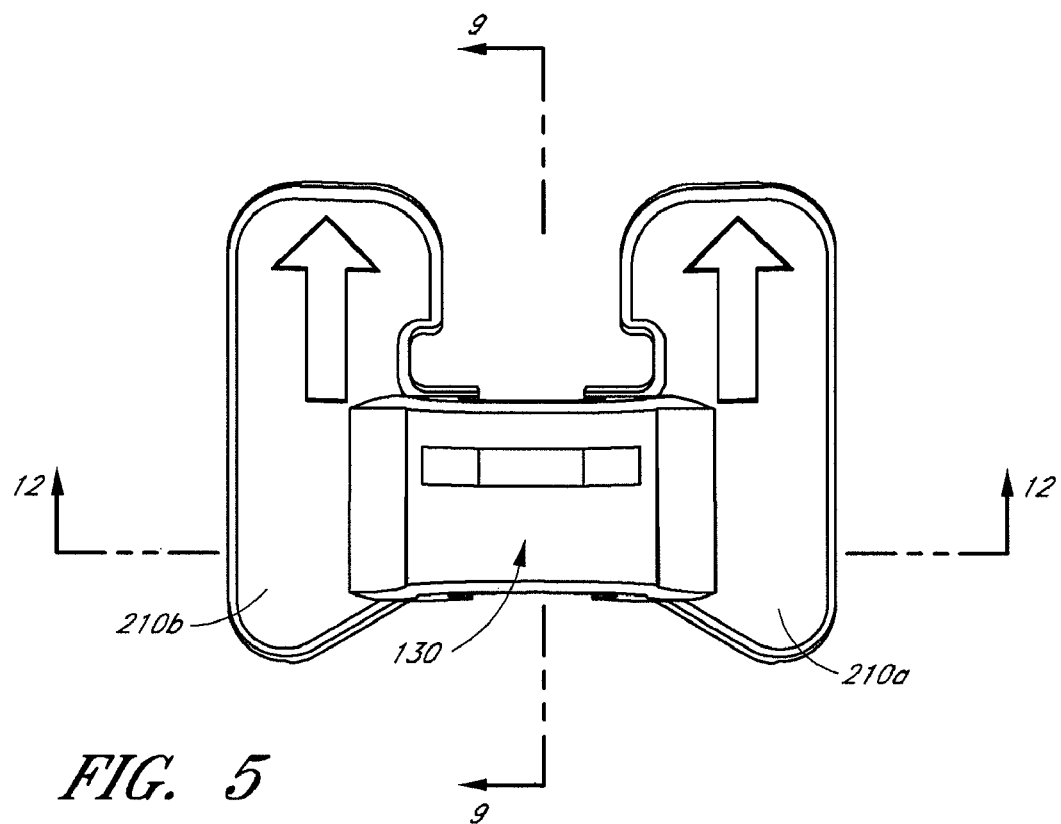
FIG. 5 is a top plan view of the retainer of FIG. 2.

An embodiment of the retainer 120 is described with reference to FIGS. 5-12. FIG. 5 is a top plan view of the retainer 120 which inhibits rotation of an installed medical article as well as arrests movement of the medical article at least in part due to the barbs 136a,b,c of the insert 135 gripping the medical article. In embodiments, the retainer 120 arrests movement in the longitudinal, lateral and transverse directions.

Figure 6:
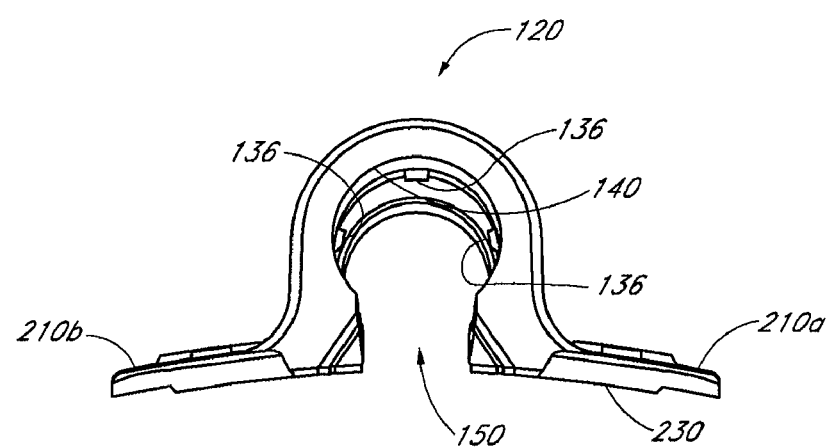
FIG. 6 is a rear side view of the retainer of FIG. 5.
Figure 7:
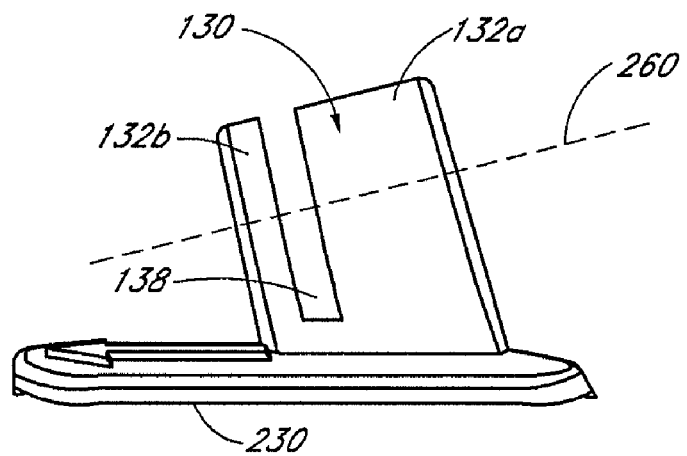
FIG. 7 is a side view of the retainer of FIG. 5.
Figure 8:
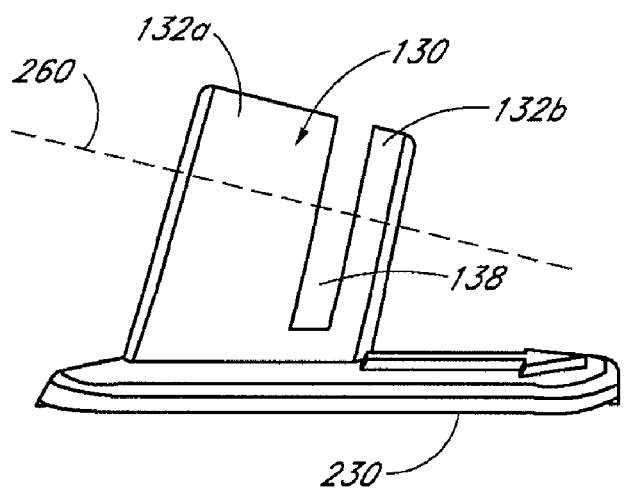
FIG. 8 is a view of the other side of the retainer of FIG. 5.

FIG. 6 is a rear side view of the retainer 120 of FIG. 5 and illustrates a body member 130 and footings/side mounting wings 210(a), 210(b) that extend in a lateral direction from either side of the body member. As shown in FIGS. 7 and 8, the body member 130 is elongated in the longitudinal direction and comprises a generally parallelepiped shape. It is advantageous for the longitudinal dimension of the body member 130 to be sufficiently long to provide stability to the retained portion of the medical article along its length. In this way, the longitudinal length of the retained portion is sufficient to inhibit the rocking of the medical article within the retainer 120. Also, the lateral dimension of the body member 130 of the retainer desirably allows the healthcare provider to easily and naturally grip the body member.

With reference to FIG. 6, the inner side of the body member 130 faces towards the patient's skin when in use and preferably defines an inverted central channel 140. The inverted channel 140 extends on the underside of the body member 130 in a longitudinal direction for receiving a section of the medical article in the illustrated embodiment. The body member 130 further includes a radial groove 290 (see FIG. 9) in the surface of the channel 140 and sized so as to receive the insert 135. The insert may be separately manufactured from the body member 130 and subsequently incorporated into the retainer 120. The insert 135 may also be integrally manufactured with the body member of a material that has properties sufficient to pinch or compress the retained portion of the medical article. In the latter embodiment, the insert 135 and body member 130 form a unitary structure.

The channel 140 and insert 135 are capable of receiving a portion or length of the medical article and are generally configured to house, to preferably grip, and to secure this portion of the medical article. In the illustrated embodiment (see FIGS. 5 through 8), the central channel 140 has a generally semi-circular cross-sectional shape with the barbs 136a, b,c extending into the channel 140.

An inner surface contour of the central channel 140 preferably is selected depending on the geometry of the portion of the medical article to be retained. For example, in a retainer 120 that is configured to retain a portion of a medical article that has a constant outer diameter, the central channel 140 preferably has a constant radius along its length. In contrast, in a retainer 120 configured to retain a portion of a medical article that has a tapering outer surface, the central channel 140 preferably has a tapering inner surface and a radius that varies along the channel length. In the illustrated embodiment, the medical article to be retained comprises a slight taper, and the illustrated retainers comprise a corresponding taper. Additional embodiments of the central channel 140 of the retainer can comprise a plurality of different radii and/or tapering regions. By matching the inner surface contour of the central channel 140 to the outer surface of the secured portion of a medical article, a more effective securement may be achieved. In addition, effective securement can also be achieved by the engagement of the insert 135 of the retainer with the medical article. One or more of the barbs 136a,b,c can grip the medical article to inhibit movement of the medical article relative to the retainer. In certain embodiments, one or more inserts can be configured within the channel.

Figure 11:
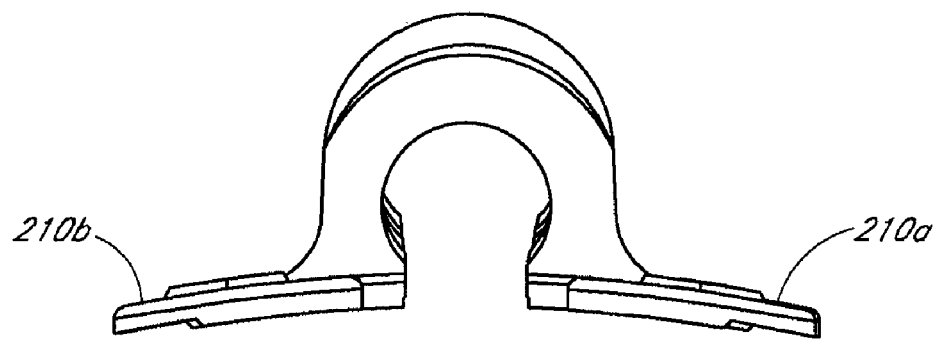
FIG. 11 is a front side view of the retainer of FIG. 5.
Figure 12:
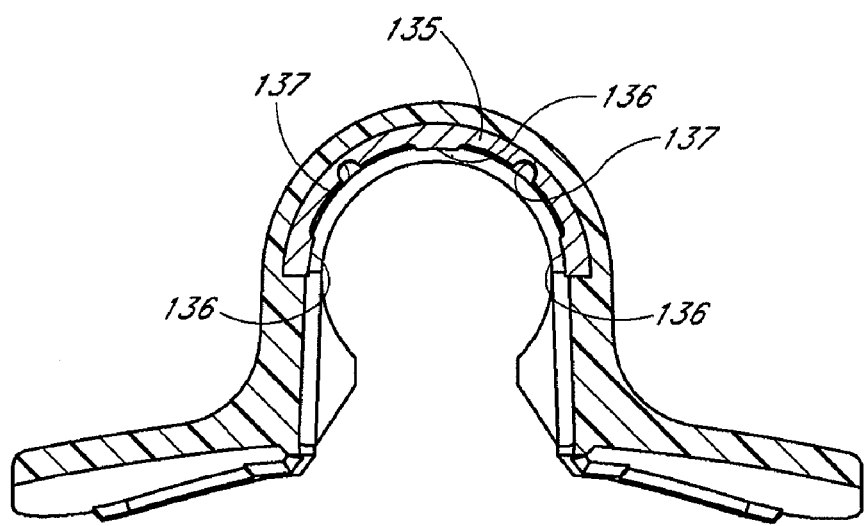
FIG. 12 is a cross-section view of the retainer taken along section 12-12 of FIG. 5 and illustrates the insert disposed within a groove in the retainer with barbs or teeth extending into the channel.

As shown most clearly in FIGS. 6 and 11, the lower side of the retainer 120 includes an access or lower opening 150. In some embodiments, the lower opening 150 has generally tapering sides along the longitudinal axis to match generally the shape of the medical article. In other embodiments, the lower opening 150 has generally parallel sides while the channel 140 is tapered to match generally the shape of the medical article. The lower opening 150 may include contouring (e.g., chamfers) along its periphery in order to guide the medical article into the central channel 140 when inserting the medical article into the retainer 120.

The illustrated retainer 120 further comprises at least one retention surface 165(a), 165(b) disposed on a lower side of the inverted channel 140. The retention surface holds at least a portion of the retained medical article within the channel 140 and hence away from the patient's skin. This support can be provided by, for example, an adhesive, a region of the inverted channel which provides a degree of snap-fit with the retained medical article, two or more regions of the inverted channel which provide a degree of snap-fit with the retained medical article, or a combination of the adhesive and a region of snap-fit. For example, the insert 135 can provide a degree of snap fit. The adhesive can be located on one or more surfaces of the retainer 120 that contact the medical article. For example, the adhesive could be located on the surface of the inverted channel or on the insert 135.

The present embodiment of the retainer 120 includes multiple pairs of retention surfaces 165(a), 165(b). The corresponding retention surfaces 165(a), 165(b) of each pair lie on opposite sides of the access opening 150 from each other. In this embodiment, the retention surface 165(a) is a portion of the surface that defines the central channel 140 and is located on the lower side of the central channel 140. The retention surface 165(a) is located to one side of the central axis. The other retention surface 165(b) is a portion of the surface that defines the central channel 140 and is located on the lower side of the central channel 140. The retention surface 165(b)

is further located to the side of the central axis that is opposite to the retention surface 165(a). Once the medical article is placed in the central channel 140, the retention surfaces 165(a), 165(b) each hold a portion of the retained section of the article within the channel 140. While multiple retention surfaces are illustrated, either retention surface 165(a), (b) can be individually employed in variations of the present retainer and still support the medical article within the channel 140.

Figure 9:
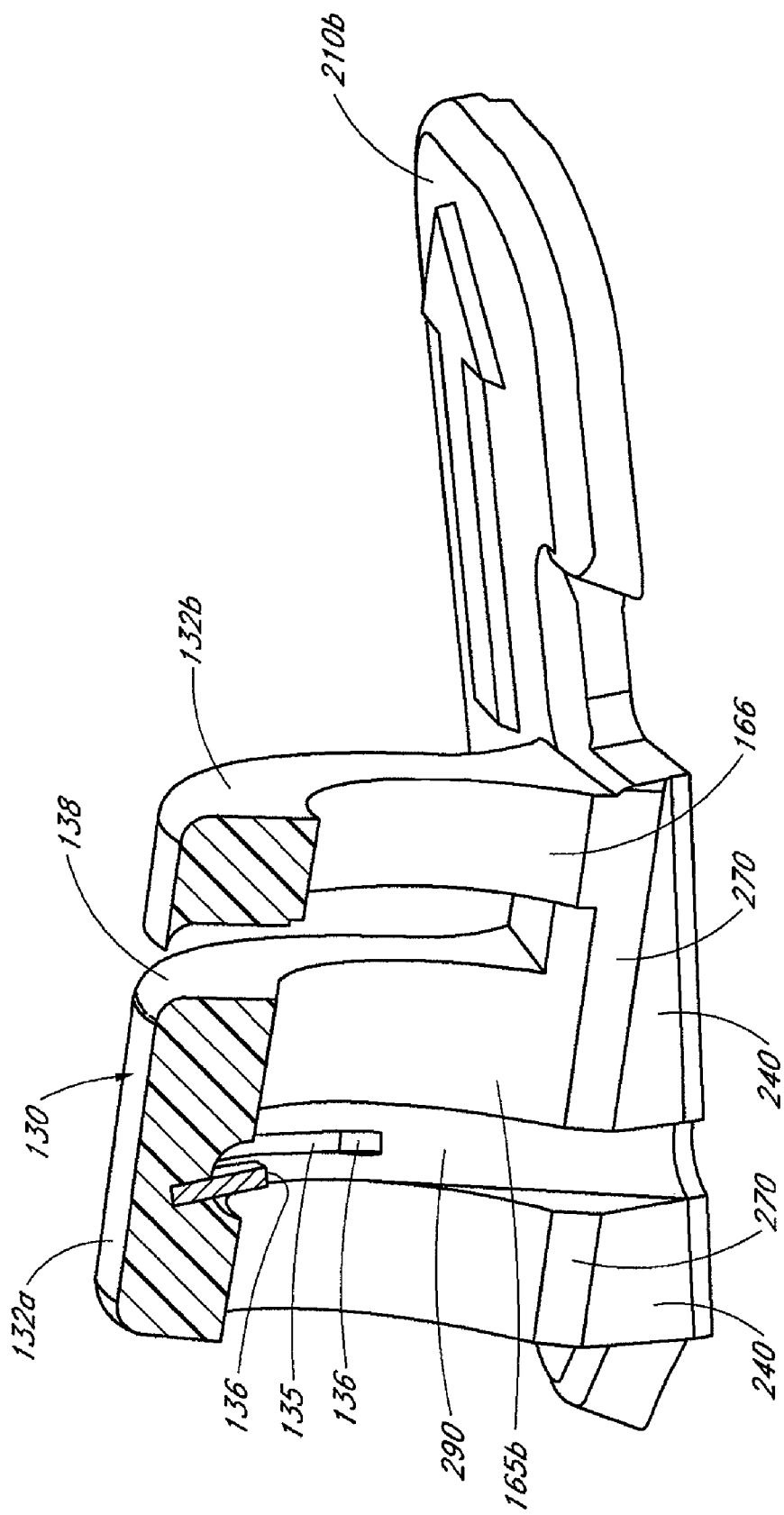
FIG. 9 is a cross-section view of the retainer taken along section 9-9 of FIG. 5.

As can best be seen in FIG. 9, the retention surface 165(a) may comprise an inwardly extending portion 166 which may serve to narrow the width of the cavity at the distal end so as to serve as a stop against which a portion of the retained medical article may abut, in order to inhibit further distal translation of the retained medical article along into the channel.

The retainer 120 comprises at least one insert 135 that is disposed on the retainer and in a wall of the channel 140. The retainer 120 may include a groove 290 or slot configured to receive the insert 135. In certain embodiments, the retainer 120 may be formed by an insert molding process in which the insert 135 is inserted into a mold and the retainer 120 formed around the insert 135. In other embodiments, however, alternate methods of fabrication may be used. For example, an integral molding process may be utilized to form the retainer 120, in which the insert 135 may comprise metal or plastic of sufficient strength to perform the desired retention function. The remainder of the retainer 120 may comprise the same material as the insert 135, but preferably comprises a softer material. Pressure can be provided by the insert 135 to hold the medical article within the retainer 120. The insert 135 bites into the outer surface of the medical article. Thus, the insert 135 is desirably made from a harder material than the material of the medical article to be retained within the retainer. In certain embodiments, the insert 135 may comprise a metal or ceramic material. In other embodiments, however, the insert 135 may comprise a relatively hard plastic, such as a polycarbonate, while the retained medical article comprises a comparatively soft plastic, such as polypropylene.

In the illustrated embodiment, the walls of the central channel 140 extend through an arc that is approximately 270°. The length of such an arc provides a snap-fit securement between the central channel 140 on the body member 130 and the secured portion of the medical article. In this way, the medical article can be placed in position prior to attaching the securement device 100 to the patient without concern that the medical article will shift while the healthcare provider is attaching the device 100 to the patient.

In the illustrated embodiment, as best seen in FIG. 9, chamfered surfaces 240 are formed on the underside of the retainer body 130 along one of the lower edges of the access opening 150. A second set of chamfered surfaces 240 are formed on the underside of the retainer body 130 along the other lower edge of the access opening 150. The portions of the retainer body 130 between these chamfered surfaces 240 and the retention surfaces 165 form hips 270. In other words, the hips 270 are the portion of the body 130 that is defined by a lower side of the central channel 140 (either the retention surfaces 165(a) on one side of the central axis or the retention surfaces 165(b) on the other side of the central axis), the chamfered surfaces 240, and the sides of the narrow lower opening 150. In one embodiment, the chamfered surfaces 240 on one side of the central axis are oblique to the chamber surfaces 240 on the other side of the central axis and help guide the medical article into the lower opening 150 and the central channel 140.

The retainer 120 can include a generally rigid structure (at least in comparison to foam or tape) and is principally defined by the body member 130 and the mounting wings 210(a), 210(b). The body member 130, however, preferably is somewhat flexible in nature, due both in part to its structure and to the material used to form the body member 130. Suitably rigid but flexible materials include, for example, but without limitation: plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. However, other materials, such as moldable metals, can be utilized. The body member 130 may comprise the same or different material than the insert 135.

The insert 135 may be more rigid that the body member 130 and may be harder than the retained medical article so as bite into the surface of the medical article. In the illustrated embodiment, the insert 135 comprises a metallic material, such as aluminum, steel, or the like. As discussed above, however, alternate materials may be utilized, and the necessary hardness may vary depending on the hardness of the medical article. In addition, an integral molding process may be used, as discussed above, in which a moldable metal or a hard plastic are used to form an integral, unitary structure which includes both the insert 135 and the body member 130.

The body member 130 and mounting wings 210(a), 210(b) may be integrally formed. This can be accomplished in any of a variety of ways well known to those skilled in the art. For instance, the retainer can be injection molded in order to reduce fabrication costs. The illustrated retainer 120 preferably is formed by injection molding using polyethylene or polypropylene material. The retainer, however, can comprise a non-unitary body member 130 and mounting wings 210(a), 210(b). In this manner, the body member and one or both of the mounting wings is formed separately and then coupled together. Additionally, the body member and mounting wings can have other forms and can have other orientations relative to one another. The body member 130 also can be clear or transparent to facilitate alignment of the retainer 120 with the medical article during installation.

In certain embodiments, the insert 135 may be separately formed and is subsequently assembled with the body member 130. In the illustrated embodiment, the insert 135 may be inserted through the channel 140 from below the retainer 120 and into the groove 290. In other embodiments, the insert may be molded with the body member 130.

Each mounting wing 210(a), 210(b) preferably includes a glue dam around a portion of its periphery on its underside. The glue dam restricts adhesive flow beyond an inner edge of the respective mounting wing. The outer edge of each mounting wing 210(a), 210(b) does not include the glue dam to allow any excess glue or adhesive to seep out from under the mounting wing during the manufacturing process in the lateral direction away from the retainer 120.

The body member 130 of the retainer is attached to the upper surface 170 of the anchor pad 110 via the mounting wings 210(a), 210(b), as is shown in FIG. 2. The body member is desirably secured to the upper surface of the pad by an adhesive, such as cyanoacrylate or other bonding material. One such adhesive is available commercially as Part No. 4011 from LOCTITE®.

When the anchor pads 110 are secured to the skin of the patient, the medical article is inhibited from moving substantially in either the lateral or transverse directions relative to the patient. Longitudinal movement of the medical article is inhibited by engagement between at least the insert 135 and on the medical article. The insert 135 preferably extends generally normal to the axis of the central channel 140, or may be canted forward (proximal) or backward (distal). Furthermore, the interior surfaces of the barbs 136 may be themselves oriented at an angle to the interior surfaces of the channel 140, so as to more effectively inhibit the motion of the retained body in a desired direction. In FIG. 9, it can be seen that the barbs 136 are angled slightly forward with respect to the central axis. The insert 135 can be located at or between the distal and proximal ends of the retainer 120. Moreover, multiple inserts 135 on the retainer 120 can be employed. In the illustrated embodiment, the longitudinally extending grooves 310 of the medical article may be received within the grooves 137 of the insert 135. The retention of such grooves 136 is not necessary, and certain embodiments may not include such grooves, as the barbs themselves may provide sufficient retention force.

A base surface 230 of the retainer 120 can have a concave curved shape when viewed from the front and rear sides. The degree of curvature can be varied depending on the expected location of usage or application of the securement device 100. It will be appreciated that many common sites for insertion of medical lines which require securement will be located on anatomical regions exhibiting convex curvature, such as a dorsal side of a hand, a arm, a leg, a contact surface, etc. By providing a concave bottom profile to the retainer 120, the retainer will rock less once placed upon the patient via the anchor pads 110(a), 110(b).

FIGS. 7 and 8 are side views of the retainer 120 of FIG. 5. As illustrated in FIGS. 7 and 8, an axis 260 of the central channel 140 lies at an angle with respect to the base surfaces 230 of the retainer 120. The desired angle between the medical article and the patient is created by angling the axis 260 of the central channel 140. This angle is selected in order to align the axis 260 of the channel 140 of the retainer with the desired incident angle with which the medical article is to contact the skin of the patient. A variety of different angles can be used, ranging from 0° to 45°, and more preferably from 5° to 25°. For instance, for the securement of intravenous catheters, it is desirable for the angle of incidence of the catheter to the skin of the patient to be between about 7° to about 15°. For the securement of arterial catheters, it is desirable for the angle of incident of the catheter to the skin of the patient to be about 12.5°. By angling the axis 260 of the channel 140 at the desired angle, which will depend upon the particular securement application (e.g., securing an arterial catheter, an intravenous catheter, etc.), the proper angle of incidence for a catheter can be maintained.

Although certain features of the retainer 120 can be specifically configured for use with a specific medical article, it will be understood by those of skill in the art that such a retainer 120 can be used with other medical articles as well. Furthermore, the retainers described herein can be modified to more effectively cooperate with various types of catheter hubs, connector fittings, and adaptors.

Figure 17:
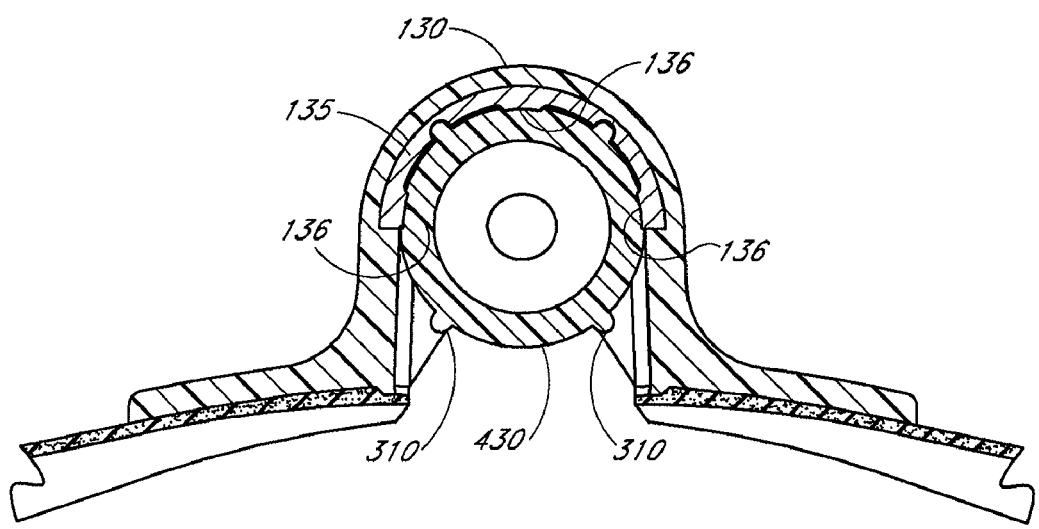
FIG. 17 is a cross-section view of the retainer taken along section 17-17 of FIG. 16 and illustrates longitudinal ridges on the outer surface of the medical article disposed within grooves in the insert and with the barbs or teeth of the insert gripping the medical article.

As shown in FIG. 1A, in certain embodiments the grooves 137 may be circumferentially located about the axis of the central channel 140 to correspond with the longitudinal ridges 310 of the medical article. In this way, the grooves or notches 137 limit the rotation of the medical article when the medical article is installed in the retainer 120 (see FIG. 17). In such embodiments, each longitudinal groove 137 preferably has a lateral width sufficient to receive the longitudinal ridges 310 of the medical article.

Figure 10:
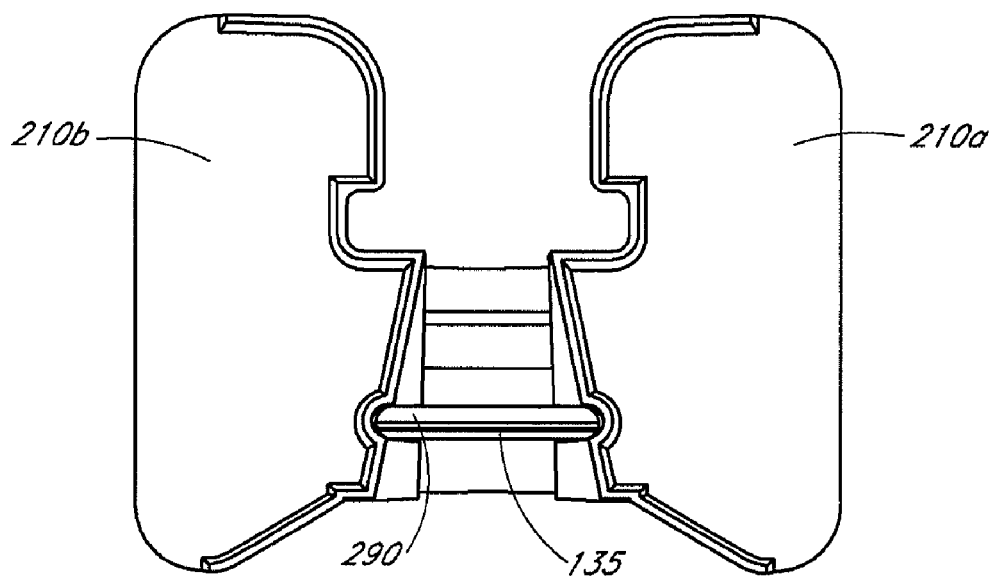
FIG. 10 is a bottom plan view of the retainer of FIG. 5 and illustrates that the distance between the side mounting wings varies in the region of the retainer.

FIG. 10 is a bottom plan view of the retainer 120 and illustrates that the distance between the side mounting wings 210(a), 210(b) varies in the region of the retainer 120 so as to facilitate the ingress of a medical article having a slightly tapered shape.

Medical Articles

Figure 13:
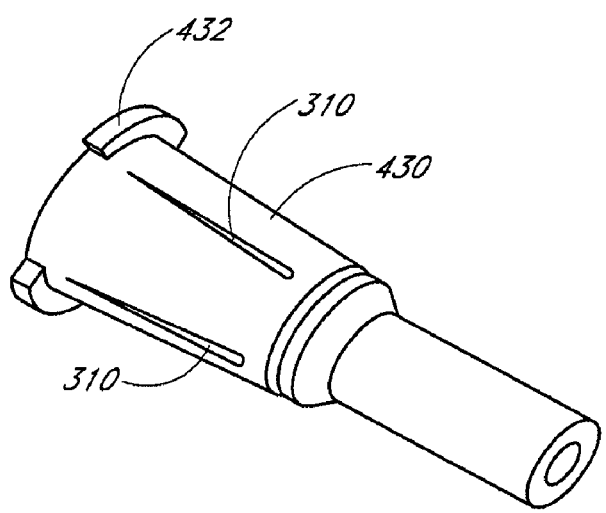
FIG. 13 is a perspective view of an example of a medical article which the securement device of FIG. 1 can be used.

An exemplary medical article for use with the embodiment of the securement device described above will now be described with reference to FIG. 13. The medical article can be a single medical article or a combination of one or more medical articles. Such medical articles can be or include, for example, but without limitation, connector fittings, catheters, catheter hubs, catheter adaptors, fluid supply lines, or other similar articles. FIG. 13 is a perspective view of a catheter hub 430.

As seen in FIG. 13, the catheter hub 430 has at least two longitudinal ridges 310 disposed upon the outer surface of the catheter hub 430. It may be advantageous for the ridges 310 to extend completely along the length of the catheter hub 430. Those of skill in the art will recognize that the ridges 310 need not have any particular shape or longitudinal length. Additionally, the ridges need not have the same shape. In alternate embodiments, the medical article may not comprise ridges, as noted above. For example, the pressure exerted by the insert 135 on the retained portion of the medical article can be sufficient to arrest rotational movement of the medical article in the retainer 120.

Still referring to FIG. 13, the catheter hub 430 includes a body that, in the illustrated embodiment, is configured as a catheter hub and has a generally conical shape and tapers from a large radius to a smaller radius along its length. In the illustrated embodiment, the catheter hub 430 comprises four ridges 310 equally spaced about the circumference.

The catheter hub 430 also can include an external screw thread 432 on the outside of the conical body near the end with the larger radius. The screw thread 432 can be used in association with a spin nut of a connector fitting in order to securely interconnect the connector fitting and the catheter hub 430.

Operation

An exemplary process for coupling a medical article with the securement device described above will now be described with reference to FIGS. 14 through 17. In order to illustrate more clearly the interaction between the retainer 120 and the catheter hub 430 in this embodiment, the anchor pads 110(a), 110(b) of the securement device 110 are illustrated as detached from the retainer 120. In accordance with the preferred embodiment, however, the entire securement device 100 is assembled in accordance with the above-description (e.g., the mounting wings 210 are attached to the anchor pads and the insert 135 is disposed within the retainer body) and is sterilized before use.

Figure 14:
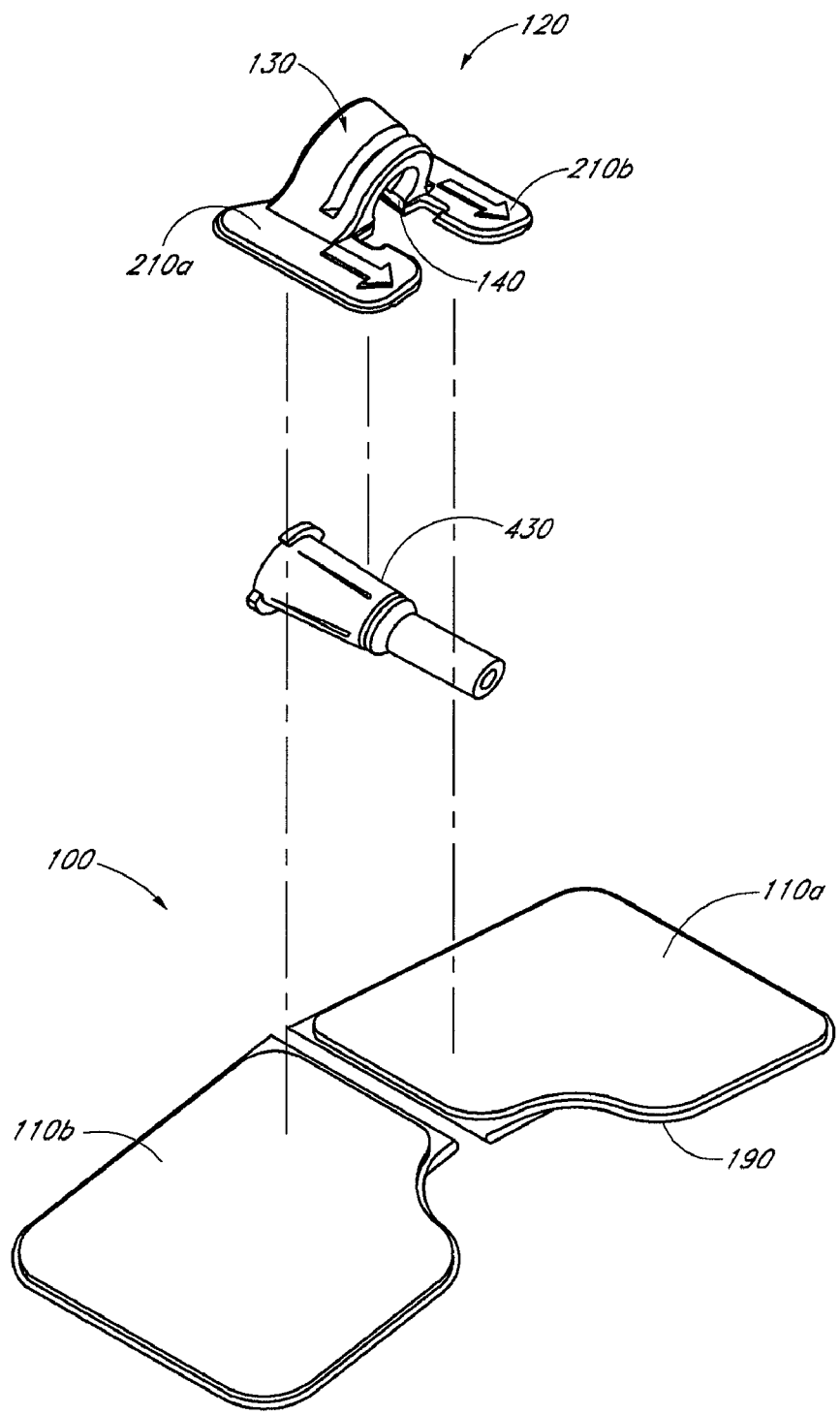
FIG. 14 is an exploded, perspective view of the medical article of FIG. 13 aligned with the anchor pad and the retainer of FIG. 1.

FIG. 14 is a perspective view of the catheter hub 430 and retainer 120, both aligned with the anchor pad 110(a), 110(b) and the retainer 120. Healthcare provider can secure a medical line and the medical articles to a patient using the above-described securement device 100 or a readily apparent modification thereof. The healthcare provider aligns the central channel 140 of the retainer 120 over the adaptor or catheter hub 430.

Figure 15:
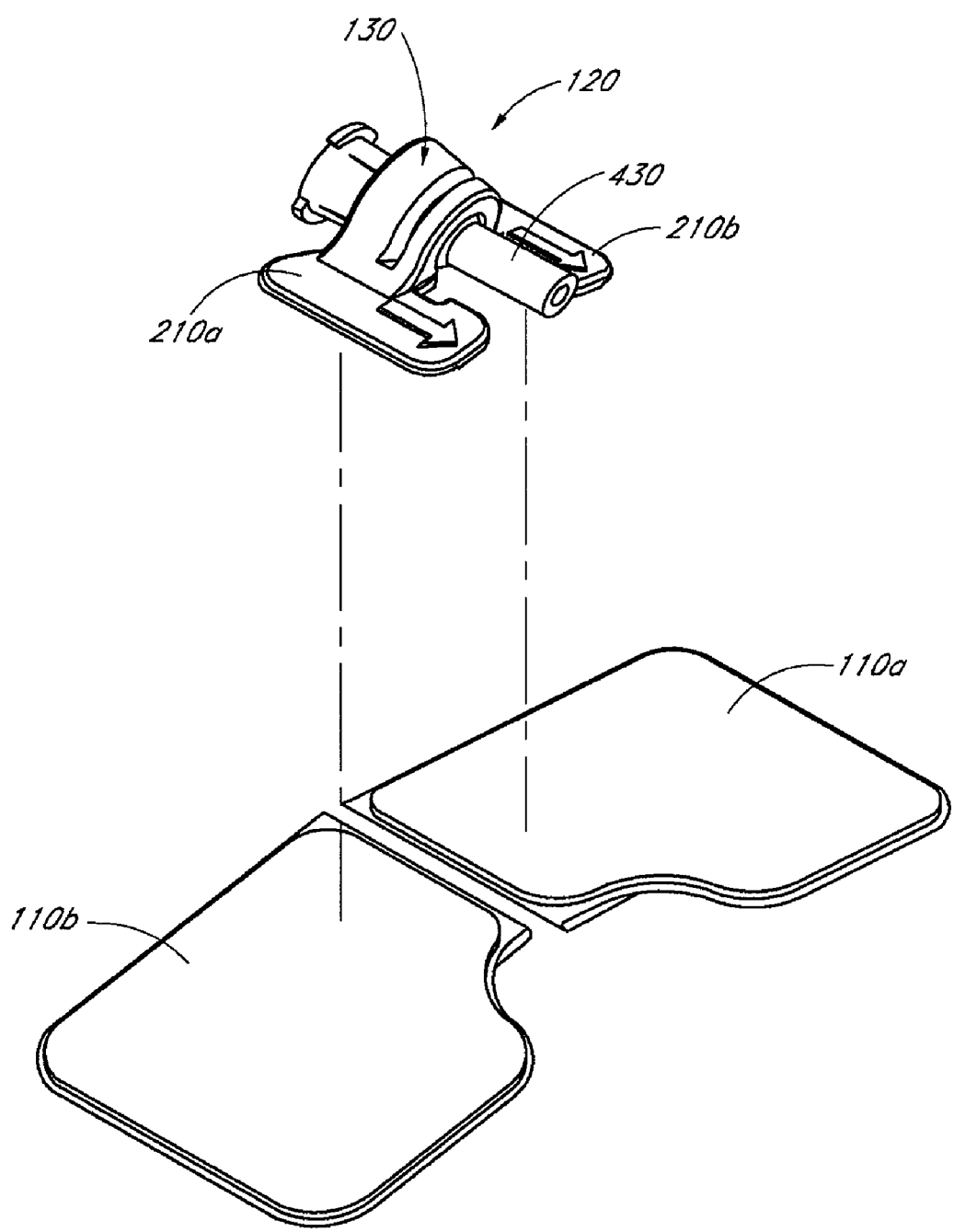
FIG. 15 is an exploded, perspective view of the medical article being inserted into the retainer of FIG. 1.

FIG. 15 is a perspective view of the catheter hub 430 with the catheter hub being inserted into the retainer 120. The lower opening 150 in the retainer 120 is pressed over the catheter hub 430 whereby the catheter hub fitting slides into the central channel 140 and the insert 135 of the retainer 120. The barbs 136a,b,c of the insert 135 preferably grip the outer surface of the catheter hub 430 so as to inhibit longitudinal movement of the catheter hub 430 relative to the retainer 120.

The ridges 310 of the catheter hub 430 preferably form one or more longitudinally extending members as shown in the illustrated embodiment. The ridges 310 fit into one (or more) of the grooves 137 in the insert 135. In addition, the body of the catheter hub 430 generally lies within the central channel 140 of the retainer. When guided through the lower opening 150 by the healthcare provider, the insert 135 will spread open slightly to allow the body of the catheter hub 430 to enter and lie within the central channel 140 of the retainer 120. The lower gripping teeth or barbs 136b and 136c of the insert 135 will then snap back against the catheter hub and bite against the outer surface inhibiting longitudinal migration of the catheter hub 430 through the central channel 140 of the retainer 120. The barbs 136 may further inhibit rotation of the medical article.

Figure 16:
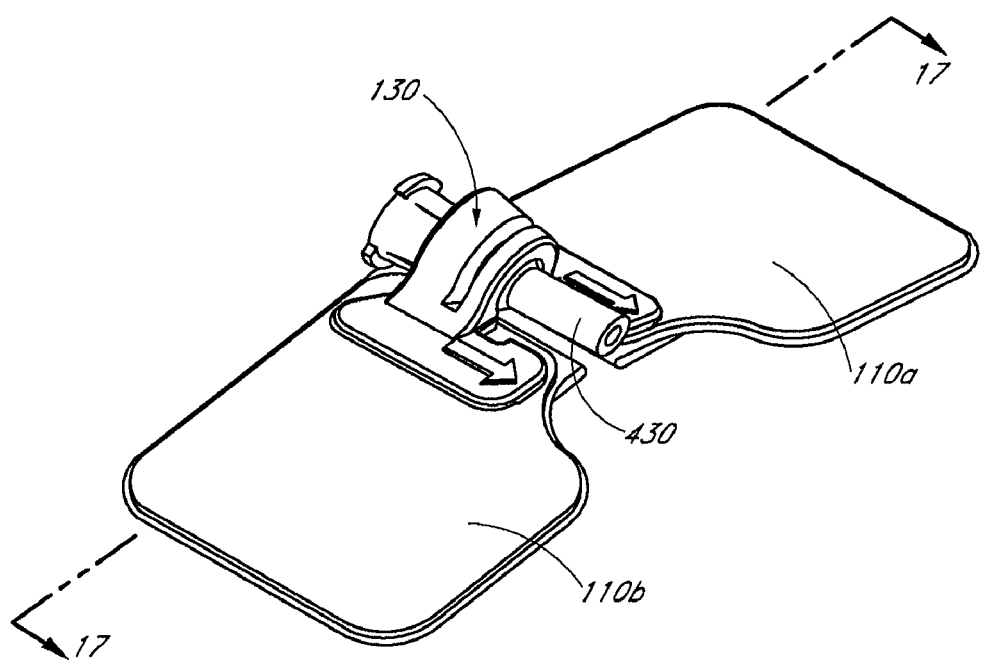
FIG. 16 is a perspective view of the medical article secured to the securement device of FIG. 1.

FIG. 16 is a perspective view of the retainer 120 attached to the anchor pads 110 and securing the catheter hub 430 therein. Once the catheter hub or other medical article enters the lower opening 150 of the retainer 120, the anchor pads 110(a), 110(b) are secured to the patient. The central channel 140 of the retainer surrounds an arc length of more than 180 degrees of the medical article. This inhibits any transverse or lateral motion of the medical article relative to the retainer 120. The catheter hub can be inserted into the retainer either before or after the fitting connector is attached to the hub.

The healthcare provider can first remove one portion of the release liner 180 from the anchor pad 110 by gripping the pull tab 190 and pulling the liner 180 away from the lower surface 160 of the anchor pad 110. This exposes the adhesive layer of the anchor pad, which can then be applied to the skin of the patient near the site where the healthcare provider desires to secure the medical article. The adhesive layer of the second anchor pad which is located in a lateral direction from the first anchor pad can be similarly exposed. The remainder of the release liner 180 for the first and second anchor pads can then be removed and the anchor pad fully attached to the skin of the patient. As a variation, the release liner on one anchor pad can be pulled away and the anchor pad can be fully attached to the patient before attaching the second anchor pad to the patient.

ALTERNATE EMBODIMENTS

As noted above, the embodiments of the retainer discussed above have been described with respect to a retainer having an inverted channel, such that the retainer substantially overlies the medical article located between the bulk of the retainer and the patient's skin. The medical article is thus inserted into the retainer from below. However, in other embodiments, the retainer may comprise a body portion configured to retain the medical article substantially on the opposite side of the retainer from the patient's skin. The bulk of the retainer is located between the medical article and the patient's skin, so that the medical article is inserted into the retainer from above.

FIGS. 18-27 depict an embodiment of a retainer 300 having a non-inverted channel. As discussed with respect to the previous embodiment, the retainer 300 is configured to inhibit undesired translation of a retained medical article at least partially through the use of one or more barbs which abut an outer surface of the retained article. The retainer 300 may further inhibit rotation of the secured medical article.

Figure 18:
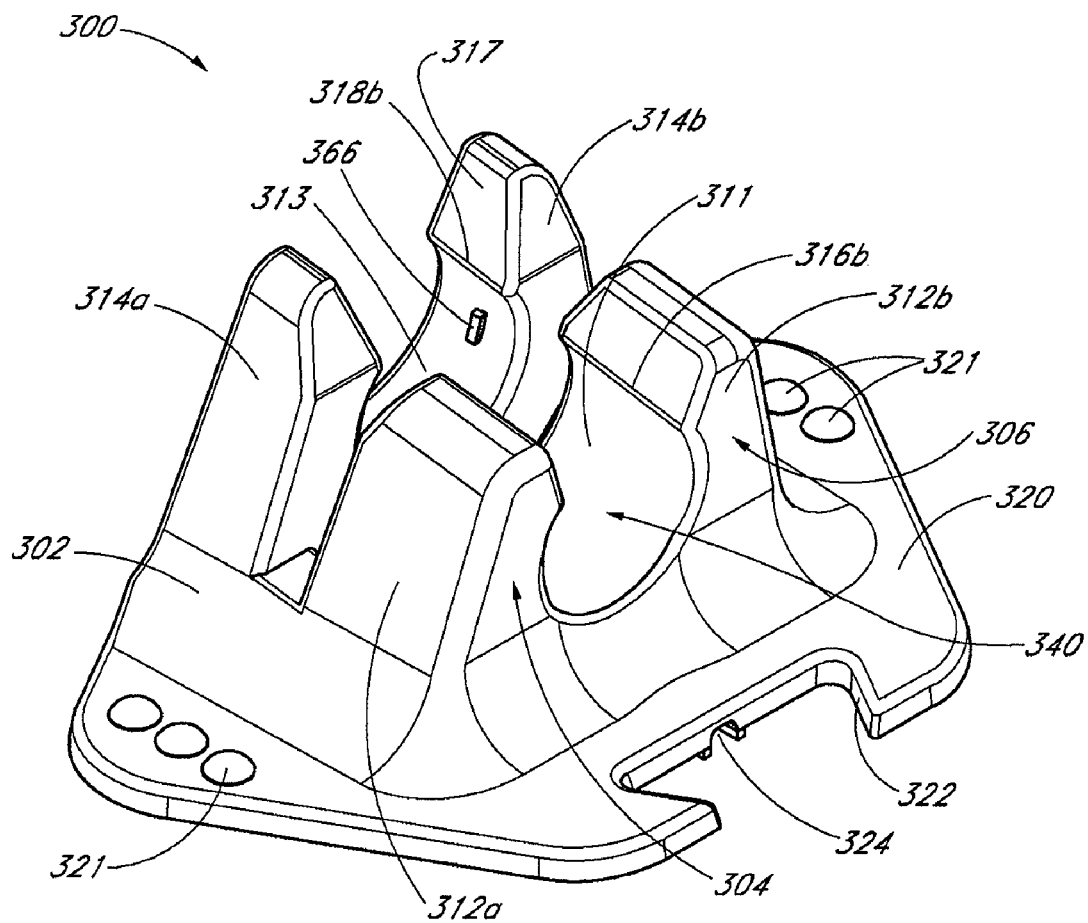
FIG. 18 is a perspective view of an alternate embodiment of a retainer.

FIG. 18 is a perspective view of the retainer 300, which comprises a central body portion 302 and a footing portion 320 extending away from the body member 302. The footing portion 320 extends not only laterally outward from the sides of the body member 302, as discussed above with respect to the previous embodiment, but also extends longitudinally forward from the proximal end of the body portion 302. The laterally extending portions of the footing portion 320 may comprise raised bumps 321 or other contouring or protrubences so as to facilitate handling of the retainer by a health care provider.

It can be seen in the illustrated embodiment that the proximal portion of the footing 320 comprises a trapezoidal notch 322 aligned with a longitudinal axis of the retainer. As can best be seen in FIG. 19, the notch 322 widens in a lateral direction moving from the proximal end of the notch to the distal end. The proximal notch 322 permits the retainer 300 to be located close to the insertion site while minimizing interference with the insertion site from the proximally extending portion of the footing 320. Depending on the nature of the medical article to be retained and the nature of the insertion site, the size of the notch 322 can be varied. In addition, the notch permits portions of the footing 320 to extend proximally further without disturbing the insertion site than would be possible without the In addition, as the bulk of the retainer 300 substantially underlies the medical article being retained, in contrast to the previous embodiment in which the body member substantially overlies the medical article, the footing 320 can extend underneath substantially all of the body member 310, as shown.

Figure 19:
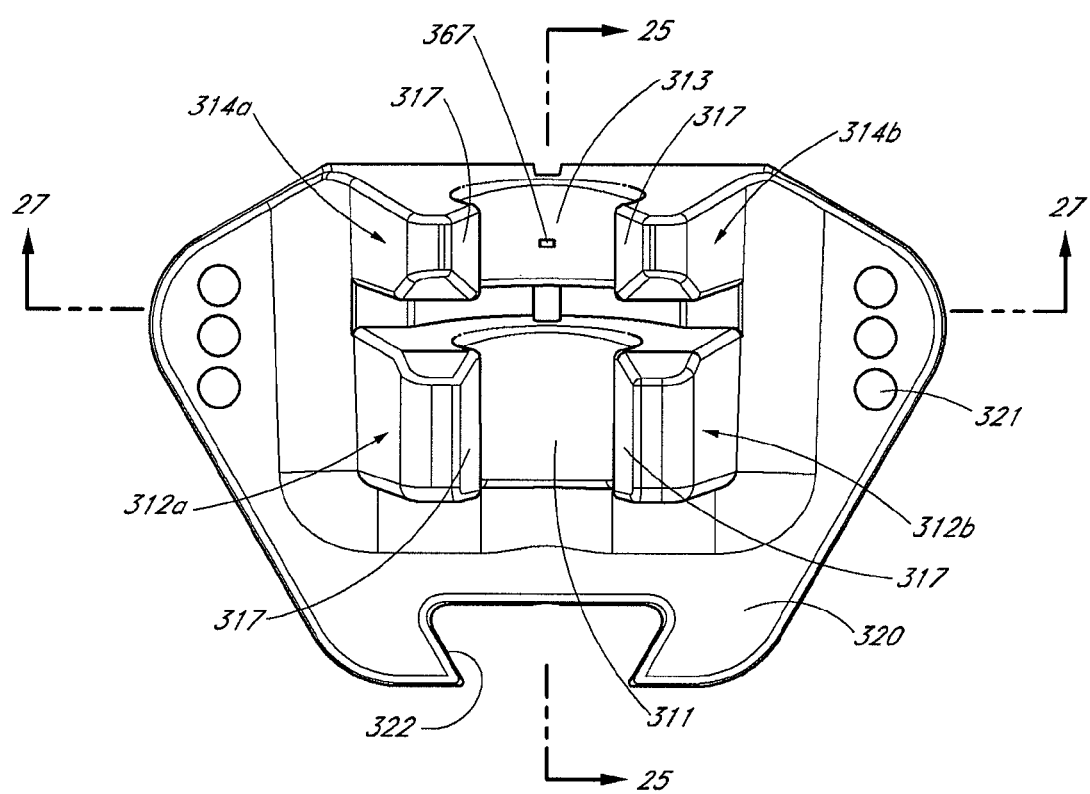
FIG. 19 is a top plan view of the retainer of FIG. 18.

It can also be seen in FIG. 18 that the footing 320 comprises a notch 324 on the underside, which may be configured to facilitate flexure of the footing 320 when the retainer 300 is positioned on an area of the patient's body having substantial curvature. In an alternate embodiment, the base surface of the footing may comprise a concave shape so as to fit more securely against a curved surface, as described with respect to the previous embodiment. In further embodiments, the underside of the footing may comprise a notch in addition to a concave surface. The notch 324 may also advantageously facilitate alignment of the retainer during placement of the retainer, as a portion of the patient's skin may be visible through the notch 324, as can be seen in FIG. 19.

Figure 20:
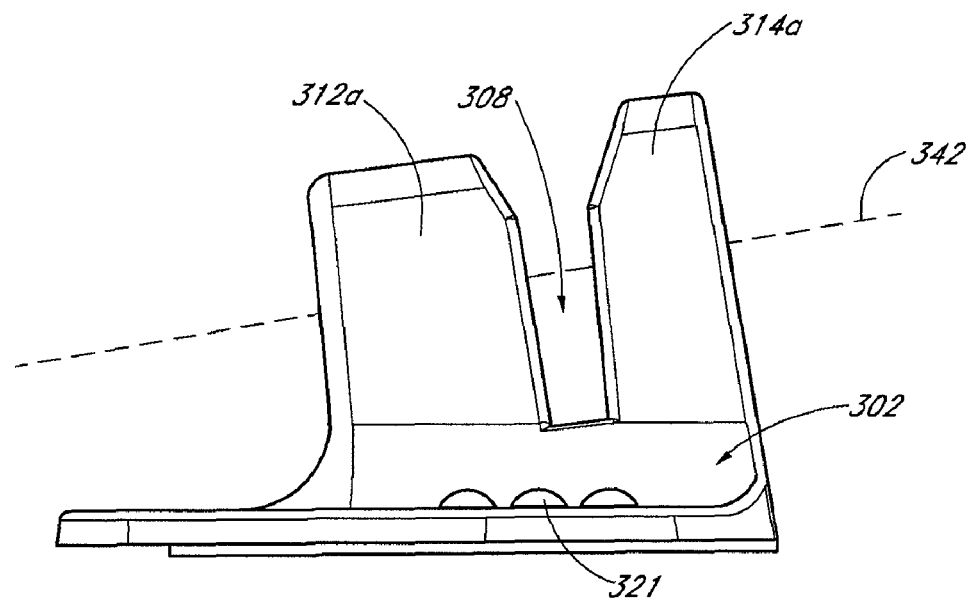
FIG. 20 is a left side view of the retainer of FIG. 18.
Figure 21:
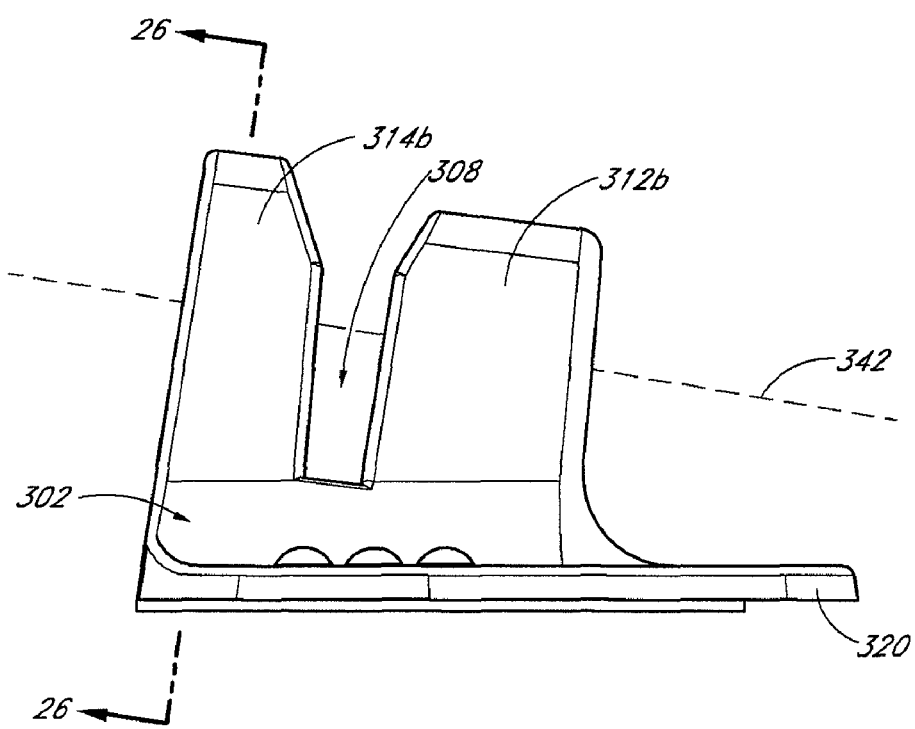
FIG. 21 is a right side view of the retainer of FIG. 18.
Figure 22:
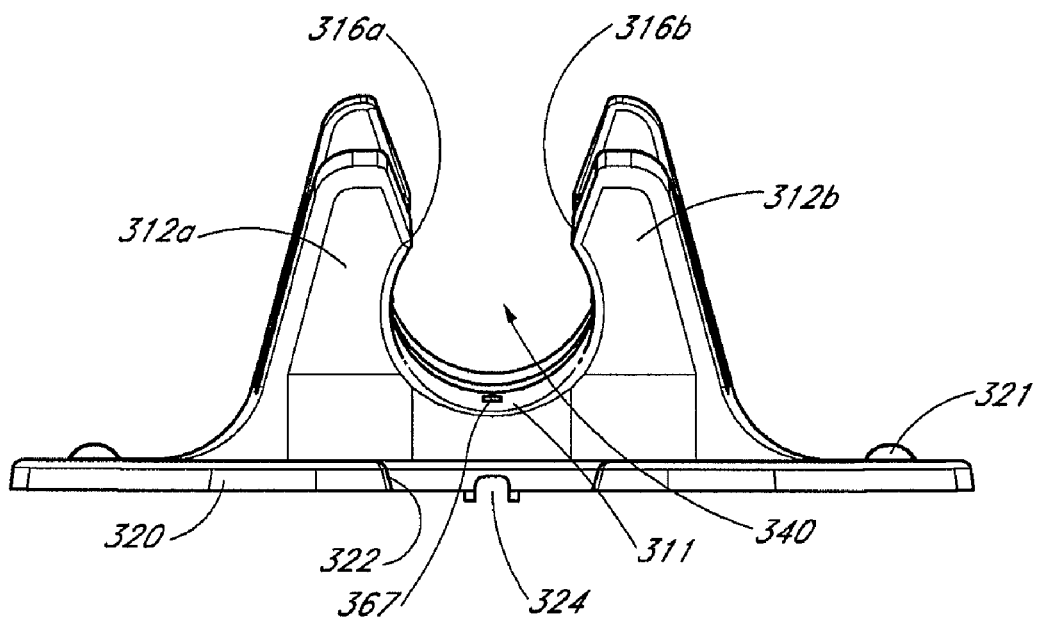
FIG. 22 is a front view of the retainer of FIG. 18.
Figure 23:
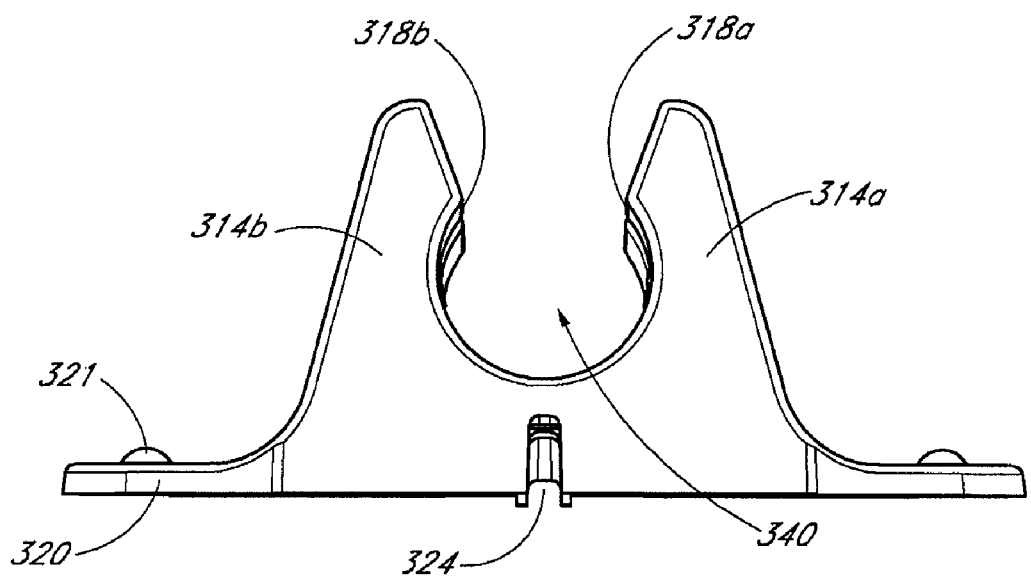
FIG. 23 is a back view of the retainer of FIG. 18.

The body portion 302 comprises a proximal pair of upstanding walls 304, 306. Each wall may comprise, as in the illustrated embodiment, a proximal portion and a distal portion separated by a slot. In the illustrated embodiment, the upstanding wall 304 comprises a proximal retaining member 312a and a distal retaining member 314a. Similarly, the upstanding wall 306 comprises a proximal retaining member 312b and a distal retaining member 314b. The proximal pair of retaining members 312a, 312b are separated from the distal pair of retaining members 314a, 314b by a slot 308, as can be seen in FIGS. 20 and 21.

The retaining members 312a,b and 314a,b extend upward in a transverse direction from the body portion 310 of the retainer 300. The upper portions of the retaining members comprise overhanging lips 316a, 316b, 318a, and 318b, which extend longitudinally along the interior sides of the retaining members. A curved surface 311 extends from the underside of overhanging lip 316a to the underside of the lip 316b, forming a retaining surface between proximal retaining members 312a and 312b. A similar curved surface 313 extends from the lip 318a to the lip 318b.

The retaining members 312a,b and 314a,b preferably comprise a resilient material, such that they can be deformed outward in a lateral direction. The retaining members also comprise chamfered contact surfaces 317 which in the illustrated embodiment are substantially planar and extend from the overhanging lips 316a,b and 318a,b to the top of the retaining members. These contact surfaces 317 are oriented such that the surface extends laterally outward and transversely upward from the overhanging lips. As will be discussed in greater detail below, these contact surfaces 317 facilitate placement of a medical article within the retainer 300.

The curved surfaces 311 and 313 define a central channel 340 extending in a longitudinal direction between the pairs of retaining members 312a,b and 314a,b. The curved surfaces 311 and 313 abut exterior surfaces of a medical article retained within channel 340, inhibiting lateral movement of the medical article. The overhanging lips 316a, 316b, 318a, and 318b, along with the inwardly-curving uppermost portions of the curved surfaces 311 and 313, releasably inhibit transverse movement of the medical article upwards and away from the retainer 300.

The particular shape of the curved surfaces 311 and 313 extending between the retaining members can be altered depending on the shape of the medical article to be retained, as discussed above with respect to FIG. 6. In the illustrated embodiment, the channel 340 has a slightly conical shape, where the cross section of the channel is slightly larger between the retaining members 314a,b than the cross section between the retaining members 312,a,b. The radius of curvature of curved surfaces 311 and 313 thus increases slightly moving in a distal direction. It will be understood, however, that shapes which are more or less conical may be used. The slightly conical shape of the central channel 340 may help to inhibit longitudinal translation of the medical article at least in the proximal direction, and may facilitate placement and securement of the medical article in the channel 340.

Figure 25:
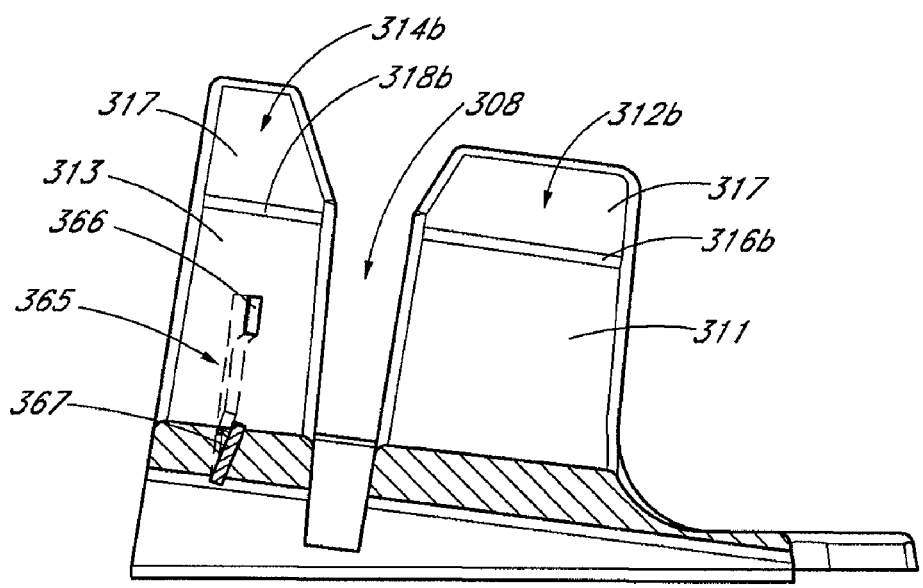
FIG. 25 is a cross-section of the retainer of FIG. 19, taken along the line 25-25, and illustrates an insert disposed so as to receive the a medical article inserted in a downward direction.

It can also be seen in FIGS. 20 and 21 that the longitudinal axis 342 of the retainer, which extends along the center of channel 340, is angled slightly downward. The medical article to be retained therein will thus be oriented at an angle to the surface of the patient's body to which the retainer is secured. The particular orientation of the longitudinal axis 342 can thus be varied in different retainer embodiments depending on the medical article intended to be retained. In FIG. 25, it can also be seen that the overhanging lips are also oriented parallel to the longitudinal axis 342. The retaining members 312a,b and 314a,b do not extend orthogonally to the base, but are rather oriented orthogonally to the longitudinal axis, and are thus tilted slightly in a proximal longitudinal direction.

Figure 24:
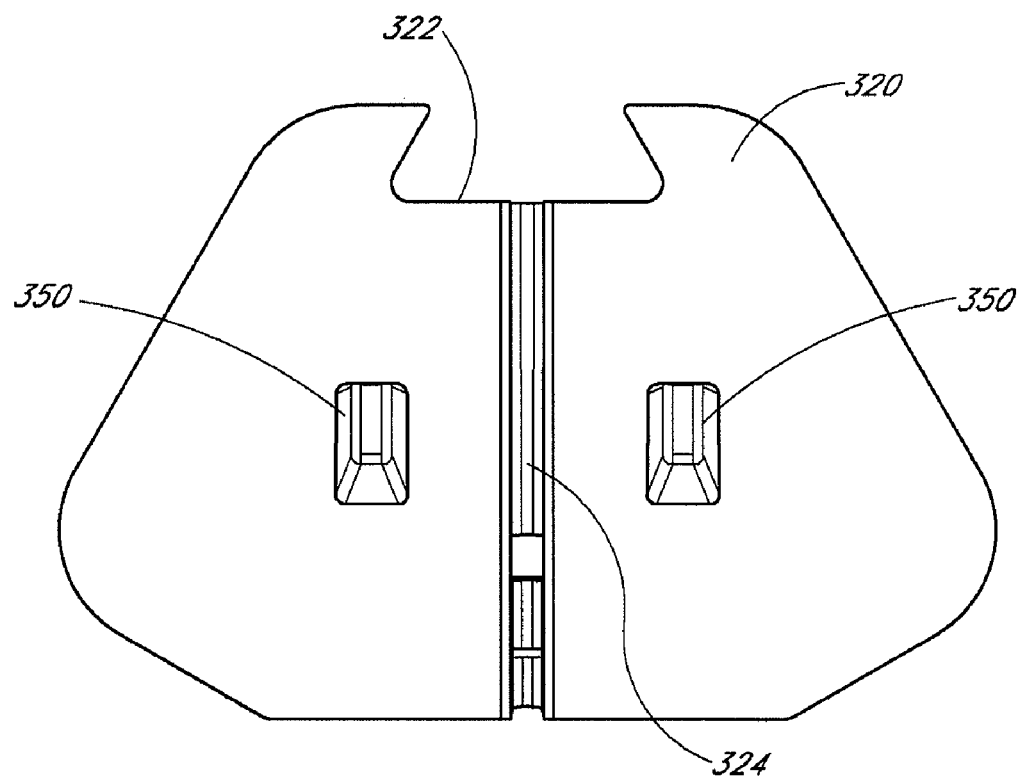
FIG. 24 is a bottom plan view of the retainer of FIG. 18.

As can be seen in FIG. 24, the retainer 300 comprises hollow portions 350 extending from the base of the retainer at least partially into proximal retaining members 312a and 312b. These hollow portions provide a lighter retainer, and also provide additional flexibility for thick retaining members such as proximal retaining members 312a and 312b. In certain embodiments, no hollow portions 350 may be provided, and in other embodiments, additional or larger hollow portions may be provided.

Figure 26:
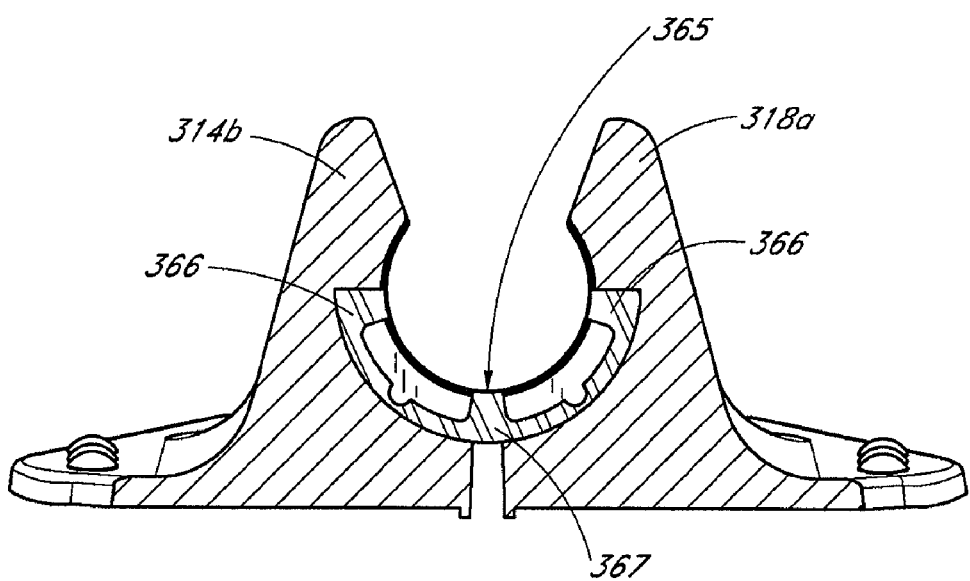
FIG. 26 is a cross-section of the retainer of FIG. 21, taken along the line 26-26, and illustrates the teeth of the insert protruding into the channel.
Figure 27:
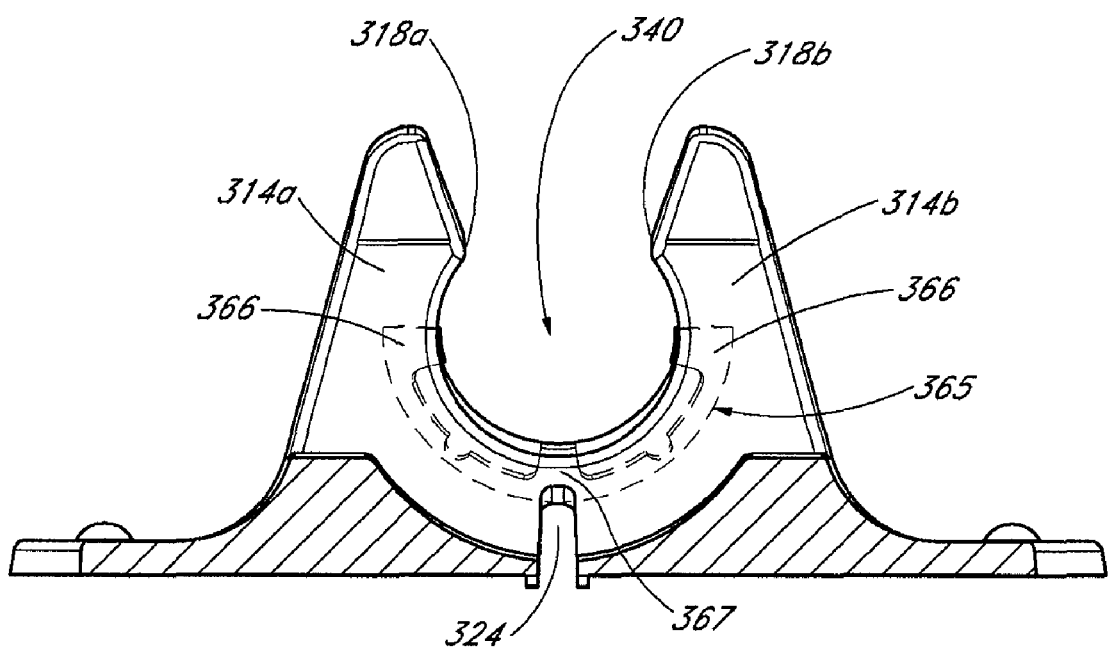
FIG. 27 is a cross-section of the retainer of FIG. 19, taken along the line 27-27.

In FIGS. 25-27, it can be seen that an insert 365 is disposed within the portion of the circular channel 340 defined by distal retaining members 314a and 314b. The insert 365 may be similar or identical to the rigid insert 135 of the previous embodiment. In the illustrated embodiment, the body portion 302 may be integrally formed about the insert 365, such that the only exposed portions of the insert may be side barbs 366 extending through the curved surface 313 and into the channel 340. In alternate embodiments, as discussed above, the retainer may comprise a groove into which a insert is secured.

The insert 365 may function essentially as described with respect to the insert of the previous embodiment, spreading outwardly to accept the medical article and the barbs scoring or deforming the surface of the medical article to prevent undesired longitudinal translation of the medical article. The side barbs 366 may also provide additional inhibition against transverse movement of the medical article relative to the retainer 300. While such additional retention may be helpful, in certain embodiments the overhanging portions of the retaining members alone may be sufficient to prevent transverse movement of the medical article, allowing greater freedom in the design of the insert. For example, if the barbs 366 are not required to inhibit transverse movement, the barbs may be located at a lower position within the channel, or fewer barbs (e.g., a single barb) may be sufficient.

In the illustrated embodiment, central portion 357 of the insert does not extend substantially into the central channel 140, and thus does not assist in the retention of the medical article. However, it will be understood that in alternate embodiments, the central portion 357 of the insert 355 may extend into the central channel and provide additional retention of the medical article.

It can also be seen in FIG. 25 that the insert 365 is generally planar and comprises barbs which are angled in a proximal direction. The slight taper of the channel 340 at least partially inhibits longitudinal translation of the medical article in a proximal direction relative to the retainer 300. By angling the barbs 366 in a proximal direction, the barb may be positioned to better inhibit longitudinal translation of the medical article in a proximal direction. It will be understood, however, that in alternate embodiments, substantially planar inserts may be utilized, as well.

Figure 28:
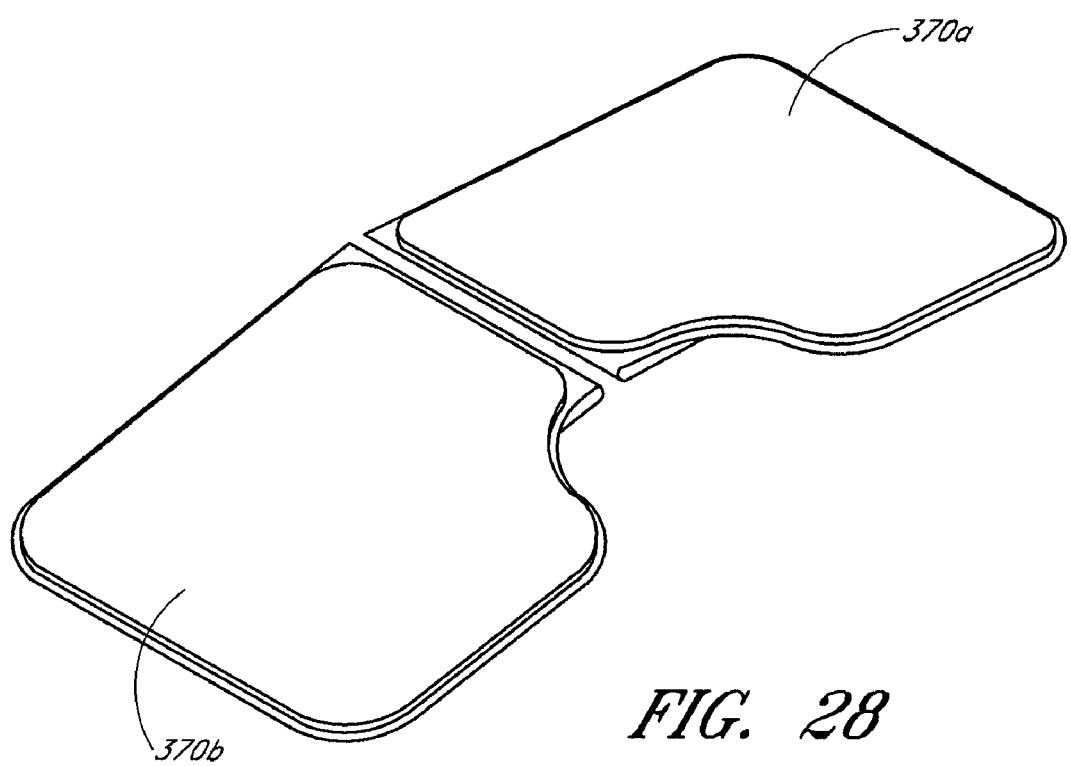
FIG. 28 is a perspective view of an anchor pad suitable for use with the retainer of FIG. 18.
Figure 29:
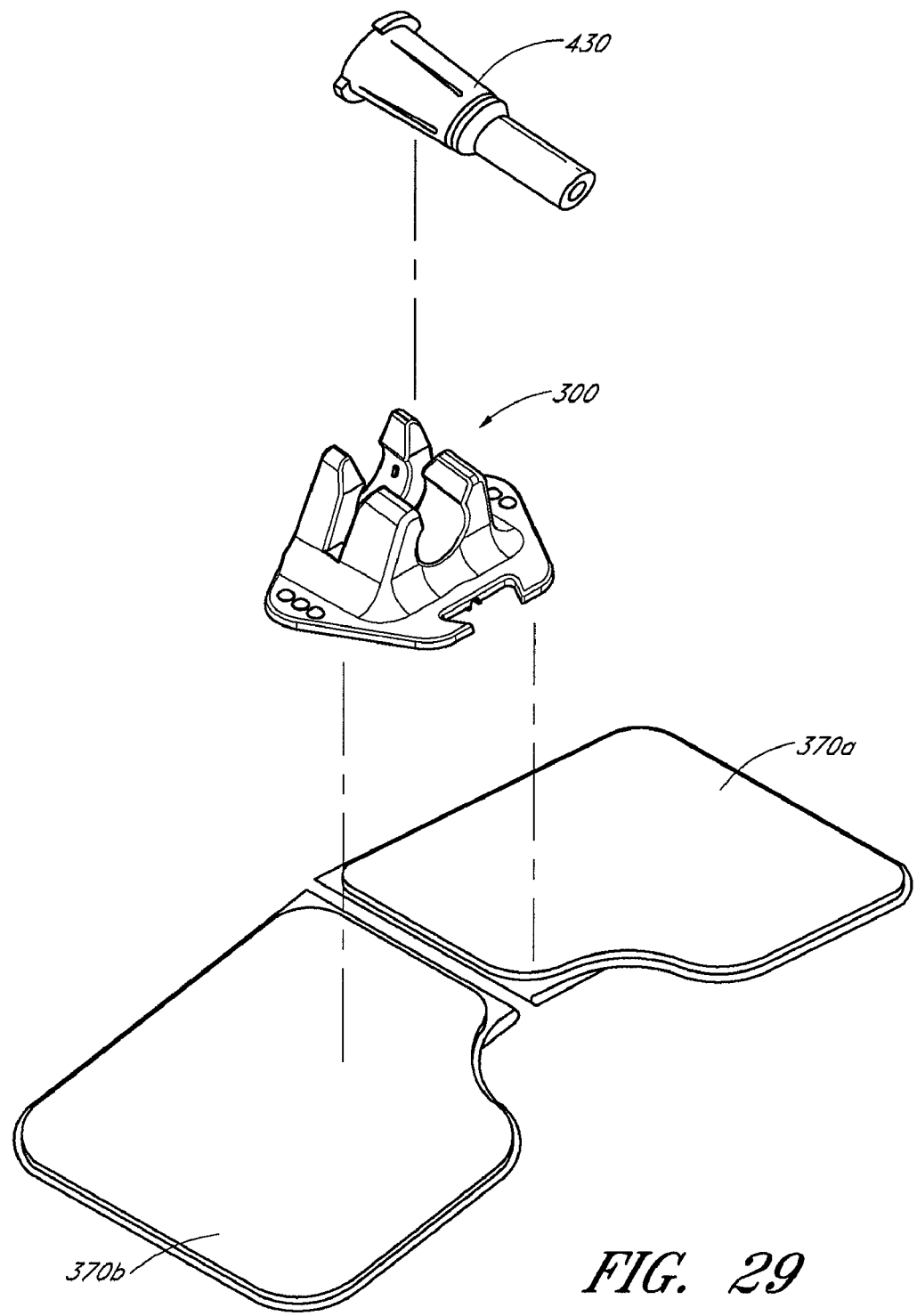
FIG. 29 is an exploded view of a securement device including the retainer of FIG. 18 and the anchor pad of FIG. 28.

The retainer 300 may be disposed upon anchor pads such as the anchor pads 110(a) and 110(b) of FIGS. 3 and 4. As can be seen in FIGS. 28 and 29, anchor pads 370a and 370b may be provided on the underside of the retainer in order to adhere the retainer to the skin of a patient. These anchor pads may be similar or identical in structure to those described above. In the illustrated embodiment, one anchor pad may be provided on either side of the groove 324 extending along the bottom of the retainer. In other embodiments, such as in embodiments comprising a concave underside, only a single anchor pad may be provided. Any suitable size or shape of anchor pad may be used.

Figure 30:
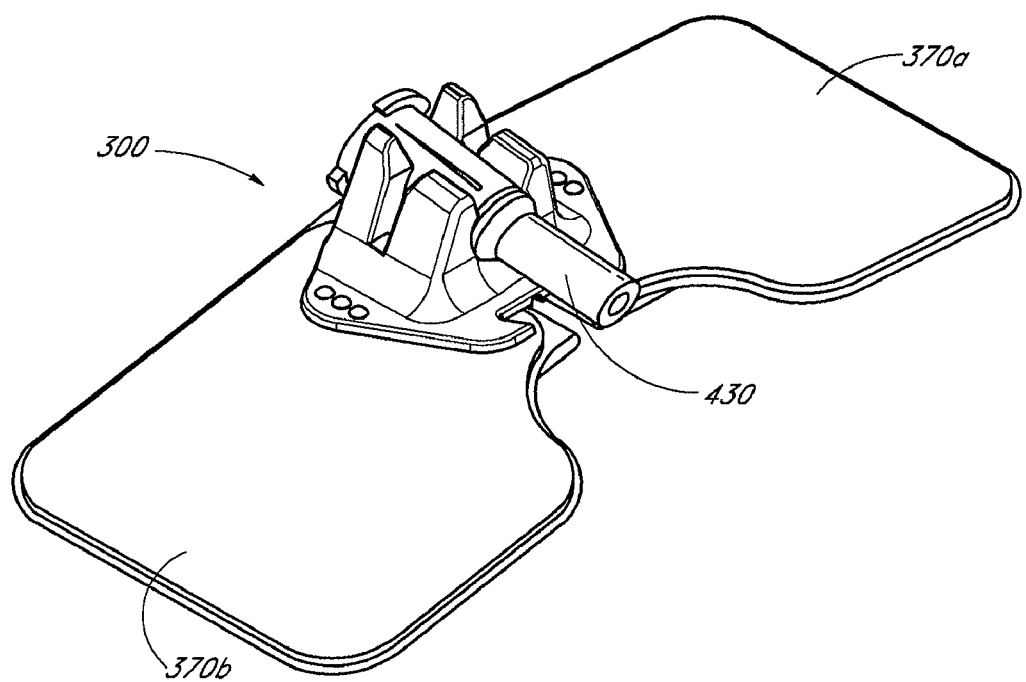
FIG. 30 is a perspective view of the assembled securement device of FIG. 29.

The operation of the retainer 300 may proceed as follows. The retainer 300 is secured to a patient's skin. A medical article, such as medical article 430 of FIGS. 29 and 30, is pressed against the retainer 300 such that the exterior of the medical article 430 abuts the contact surfaces 317 of the retainer 300. The pressure against the contact surfaces causes the retaining members to bend outward, permitting entry of the medical article between the overhanging lips and into the central channel 340 of the retainer. As the medical article enters the central channel, the barbs 366 of the insert 365 interact with the exterior surface of the medical article. Depending on the relative hardness and shape of the barbs and the medical article, the barbs may deform or score the surface of the medical article, so as to retain the medical article in place. The medical article may be removed by pulling the medical article upward so as to deform the retaining members outward and allow the medical article to be removed from the central channel.

Because the retainer 300 is positioned between the medical article and the patient, flexibility is provided with respect to the securement of the medical article. In particular, it will be understood that the medical article can be positioned within, and removed from, the retainer 300 while the retainer is secured to the patient's body. This facilitates the securement of the medical article on the patient's skin, as the medical article need not be secured within the retainer during this process. In alternate embodiments, the medical article may be secured within the retainer prior to the retainer being positioned on a patient's skin.

The various embodiments of securement devices and techniques described above thus provide a number of ways to provide safe and releasable securement for medical articles to the skin of a patient. In addition, the techniques described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and systems have been disclosed in the context of certain embodiments and examples, it will be understood by those skilled in the art that these techniques and systems may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above.

What is claimed is:

1. A retainer for securing a medical article, the retainer comprising:
   a body portion, the body portion comprising a channel extending in a longitudinal direction therethrough, said channel being configured to accept at least a portion of a medical article;
   at least one footing, the footing comprising two wing portions extending latitudinally outward from a bottom of the body portion, wherein said channel is located between the wing portions;
   at least one barb extending inwardly into said channel, said barb being configured to move independent of said body portion, said barb pressing against said medical article so as to inhibit longitudinal motion of said medical article when said medical article is placed within said channel; and
   at least one anchor configured to fit against the skin of the patient, said anchor supporting said body portion.

2. The retainer of claim 1, further comprising at least one insert, said at least one insert comprising a curved outer portion and said at least one barb, wherein said at least one barb extends inwardly from said curved outer portion, and wherein said at least one insert is retained within the body portion such that said at least one barb extends inwardly into the channel.

3. The retainer of claim 2, wherein the body portion comprises a groove configured to accept and retain the at least one insert, said at least one insert being disposed at least partially within said groove.

4. The retainer of claim 2, wherein the at least one insert comprises at least a second barb extending inwardly from said curved outer portion, said first and second barbs being spaced apart from one another and configured to retain at least a portion of the medical article therebetween.

5. The retainer of claim 1, wherein said barb is disposed so as to extend inwardly into the channel.

6. The retainer of claim 5, wherein the barb is disposed so as to also extend longitudinally towards a proximal end of the channel.

7. The retainer of claim 1, wherein the body portion comprises at least one pair of retaining members extending transversely upwards from the footing, wherein an inward surface of each of said at least one pair of retaining members cooperates to define the channel.

8. A securement device, comprising:
   a body portion, said body portion comprising resiliently deformable sidewalls which cooperate to define a channel extending in a longitudinal direction through the body portion and configured to accept at least a portion of a medical article therein, said sidewalls being deformable laterally outward to permit passage of the medical article through an opening therebetween; and
   an insert being outwardly deformable to permit entry of a portion of the medical article therein, said insert comprising at least one rigid barb extending inwardly into the channel, said barb being configured to interact with an exterior surface of the medical article to inhibit movement of the medical article relative to the body portion.

9. The securement device of claim 8, further comprising chamfered surfaces located on opposite sides of the opening between the sidewalls, the chamfered surfaces being configured to guide the medical article into the channel.

10. The securement device of claim 8, wherein the insert comprises at least a second barb, wherein said first barb is positioned on the opposite side of the channel from the second barb.

11. The securement device of claim 8, wherein the sidewalls are defined by the interior surfaces of at least one pair of retaining members, said retaining members extending transversely upward.

12. The securement device of claim 8, additionally comprising a substantially flat portion configured to be positioned adjacent the skin of a patient.

13. A securement device for retaining a medical article, said securement device comprising:
   a channel dimensioned so as to retain at least a portion of the medical article, said channel being at least partially defined by a pair of opposing walls; and
   an insert disposed within the channel, said insert comprising a first barb, a second barb, and a receiving space therebetween for retaining a portion of the medical article when said portion of the medical article is retained within the channel, wherein said first and second barbs extending inwardly into the channel, said insert being biased such that the barbs remain in a first position when no portion of a medical article is retained within the receiving space, and said barbs being movable to a second position to accommodate at least a portion of a medical article disposed within the receiving space, said barbs being farther away from a central axis of the channel than said first position.

14. The retainer of claim 13, wherein the insert comprises a notched portion to permit outward deformation of the insert when the medical article is positioned within the receiving space.

15. A retainer comprising:
   a body portion, the body portion comprising a channel extending in a longitudinal direction therethrough, wherein said body portion comprises a first material; and
   a barb, wherein a portion of said barb extends inwardly into the channel so as to deform an outer surface of a medical article retained within the channel, said barb comprising a second material, said second material being harder than said first material;

at least one footing supporting said body portion.

16. The retainer of claim 15, additionally comprising an insert, said insert comprising said first barb.

17. The retainer of claim 16, wherein the body portion is integrally formed about the insert.

18. The retainer of claim 15, wherein said insert comprises a second barb.

19. The retainer of claim 15, wherein said body portion and said insert are separately formed.

20. The retainer of claim 15, wherein the second material is harder than the outer surface of the medical article to be retained.

21. A retainer for securing a medical article, the retainer comprising:
- a body portion, the body portion comprising a channel extending in a longitudinal direction therethrough, said channel being configured to accept at least a portion of a medical article;
- at least one barb extending inwardly into said channel, said barb being configured to move independent of said body portion, said barb pressing against said medical article so as to inhibit longitudinal motion of said medical article when said medical article is placed within said channel;
- at least one insert, said at least one insert comprising a curved outer portion and said at least one barb, wherein said at least one barb extends inwardly from said curved outer portion, wherein said at least one insert is retained within the body portion, and wherein the at least one insert comprises at least a second barb extending inwardly from said curved outer portion, said first and second barbs being spaced apart from one another and configured to retain at least a portion of the medical article therebetween; and
- at least one anchor configured to fit against the skin of the patient, said anchor supporting said body portion.

22. A retainer for securing a medical article, the retainer comprising:
- a body portion, the body portion comprising a channel extending in a longitudinal direction therethrough, said channel being configured to accept at least a portion of a medical article;
- at least one barb extending inwardly into said channel and longitudinally towards a proximal end of the channel, said barb being configured to move independent of said body portion, said barb pressing against said medical article so as to inhibit longitudinal motion of said medical article when said medical article is placed within said channel; and
- at least one anchor configured to fit against the skin of the patient, said anchor supporting said body portion.

* * * * *